United States Patent [19]
Johnson

[11] Patent Number: 5,824,307
[45] Date of Patent: Oct. 20, 1998

[54] HUMAN-MURINE CHIMERIC ANTIBODIES AGAINST RESPIRATORY SYNCYTIAL VIRUS

[75] Inventor: Leslie Sid Johnson, Germantown, Md.

[73] Assignee: MedImmune, Inc., Gaithersburg, Md.

[21] Appl. No.: 290,592

[22] Filed: Aug. 15, 1994

Related U.S. Application Data

[63] Continuation-in-part of Ser. No. 813,372, Dec. 23, 1991, abandoned.

[51] Int. Cl.$^6$ .............................. A61K 39/42; C07K 16/08
[52] U.S. Cl. ...................................... 424/133.1; 424/142.1; 424/147.1; 424/159.1; 530/387.3; 530/388.15; 530/388.3
[58] Field of Search ............................ 530/387.3, 388.15, 530/388.3; 424/133.1, 142.1, 147.1, 159.1

[56] References Cited

U.S. PATENT DOCUMENTS

| | | |
|---|---|---|
| 4,659,563 | 4/1987 | Dobkin . |
| 4,717,766 | 1/1988 | Dobkin . |
| 4,800,078 | 1/1989 | Prince et al. . |

OTHER PUBLICATIONS

Tempest et al (1991, Mar.) Biotechnology 9:266–271.

Beeler et al (1989) J. Virol. 63(7):2941–2950.

Jones et al (1986) Nature 329:522–525.

Roitt (1991) "Essential Immunology", Blackwell Scientific Publications, Oxford, pp. 65–68 & 74.

*Primary Examiner*—Anthony C. Caputa
*Attorney, Agent, or Firm*—Elliot M. Olstein

[57] ABSTRACT

This invention relates to a human antibody which contains the one CDR from each variable heavy and variable light chain of at least one murine monoclonal antibody, against respiratory syncytial virus which is MAb1129 and the use thereof for the prevention and/or treatment of RSV infection.

**30 Cla

FIG. IA

```
                    5                        10
Gln Val Gln Leu Val Gln Ser Gly Ala Glu Val Lys

Gln Val Gln Leu Val Gln Ser Gly Ala Glu Val Lys
 *               *                        *   *
Glu Val Gln Leu Gln Gln Ser Gly Ala Glu Leu Val 25                        30
Ser Cys Lys Ala Ser Gly Tyr Thr Phe Asn Ser Tyr
                         *   *   *   *   *
Ser Cys Lys Ala Ser Gly Phe Asn Ile Lys Asp Tyr
                                         ─── ───
Ser Cys Lys Ala Ser Gly Phe Asn Ile Lys Asp Tyr 45                        50
Pro Gly Gln Gly Leu Glu Trp Met Gly Ile Ile Asn
                             *       *   *   *
Pro Gly Gln Gly Leu Glu Trp Ile Gly Trp Ile Asp
 *                       ─── ─── ─── ─── ───
                                             CDR
Pro Glu Gln Gly Leu Glu Trp Ile Gly Trp Ile Asp 65                        70
Ala Gln Lys Phe Gln Gly Arg Val Thr Met Thr Arg
 *   *                   ─── ─── ─── ─── ─── ───
Asp Pro Lys The Gln Gly Arg Val Thr Met Thr Arg
                         *   *   *   *       *
Asp Pro Lys Phe Gln Gly Lys Ala Ser Ile Thr Ser
─── ─── ─── ─── ─── ───

85                        90
        Glu Leu Ser Ser Leu Arg Ser Glu Asp Thr Ala

Met Glu Leu Ser Ser Leu Arg Ser Glu Asp Thr Ala
 *                       *
Leu Gln Leu Ser Ser Leu Thr Ser Glu Asp Thr Ala 105                       110
 -   -   -   -   -   -   -   -   -   -   -   -

Thr Ser Ser Phe Asp Phe Trp Gly Gln Gly Thr Thr
─── ─── ─── ─── ─── ───
      CDR 3
Thr Ser Ser Phe Asp Phe Trp Gly Gln Gly Thr Thr
```

FIG. IB

|  |  | 15 |  |  |  | 20 |  |
|---|---|---|---|---|---|---|---|
| Lys | Pro | Gly | Ala | Ser | Val | Lys | Val | Human HV3 VH |
| Lys * | Pro | Gly | Ala | Ser * | Val | Lys | Val * | "CDR Grafted" VH |
| Arg | Pro | Gly | Ala | Leu | Val | Lys | Leu | Murine 1308F VH |

|  | 35 |  |  |  | 40 |  |
|---|---|---|---|---|---|---|
| Tyr | Met * | His * | Trp | Val | Arg | Gln | Ala |
| Tyr | Ile | Tyr | Trp | Val | Arg | Gln * | Ala * |
|  | CDR 1 |  |  |  |  |  |
| Tyr | Ile | Tyr | Trp | Val | Lys | Gln | Arg |

|  |  | 55 |  |  |  | 60 |
|---|---|---|---|---|---|---|
| Pro | Ser * | Gly * | Gly | Ser * | Thr | Ser * | Tyr * |
| Pro | Glu | Asn | Gly | Asn | Thr | Val | Phe |
| 2 |  |  |  |  |  |  |  |
| Pro | Glu | Asn | Gly | Asn | Thr | Val | Phe |

| 75 |  |  |  |  |  | 80 |
|---|---|---|---|---|---|---|
| Asp | Thr | Ser | Thr | Ser | Thr | Val | Tyr |
| Asp | Thr | Ser | Thr * | Ser * | Thr | Val * | Tyr |
| Asp | Thr | Ser | Ser | Asn | Thr | Ala | Tyr |

|  | 95 |  |  |  |  | 100 |
|---|---|---|---|---|---|---|
| Val | Tyr | Tyr | Cys | Ala |  |  |
| Val | Tyr | Tyr | Cys | Ala | Tyr | Tyr | gly |
| Val | Tyr | Tyr | Cys | Ala | Tyr | Tyr | Gly |
|  |  |  |  | <<V | / | D |
|  | 115 |  |  |  |  |  |
| — | — | — | — | — |  |  |

Leu Thr Val Ser Ser

Leu Thr Val Ser Ser

FIG. 2A

```
                      5                          10
    Asp Ile Gln Met Thr Gln Ser Pro Ser Thr Leu Ser

Asp Ile Gln Met Thr Gln Ser Pro Ser Thr Leu Ser
                *                        *   *   *
    Asp Ile Lys Met Thr Gln Ser Pro Ser Ser Met Tyr 25                          30
    Ile Thr Cys Arg Ala Ser Gln Ser Ile Ser Ser Trp
                *                *       *   *   *
    Ile Thr Cys Lys Ala Ser Gln Asp Ile Asn Arg Tyr
                            CDR 1
    Ile Thr Cys Lys Ala Ser Gln Asp Ile Asn Arg Tyr 45                          50
    Gly Lys Ala Pro Lys Leu Leu Ile Tyr Asp Ala Ser
                                         *       *
    Gly Lys Ala Pro Lys Leu Leu Ile Tyr Arg Ala Asn
                *           *           *
    Gly Lys Ser Pro Lys Thr Leu Ile His Arg Ala Asn 65                          70
    Arg Phe Ser Gly Ser Gly Ser Gly Thr Glu Phe Thr

Arg Phe Ser Gly Ser Gly Ser Gly Thr Glu Phe Thr
                                     *       *   *
    Arg PHE Ser Gly Ser Gly Ser Gly Gln Glu Tyr Ser 85                          90
    Asp Asp Phe Ala Thr Tyr Tyr Cys Gln Gln Tyr Asn
                                     *       *   *
    Asp Asp Phe Ala Thr Tyr Tyr Cys Leu Gln Phe His
     *   *   *   *
    Glu Asp Met Gly Ile Tyr Tyr Cys Leu Gln Phe His

105
     -   -   -   -   -   -   -

Gly Thr Lys Leu Glu Ile Lys

Gly Thr Lys Leu Glu Ile Lys
```

FIG. 2B

|  | 15 |  |  |  | 20 |  |  |
|---|---|---|---|---|---|---|---|
| Ala | Ser | Val | GLY | Asp | Arg | Val | Thr – Human K102 VL |
| Ala | Ser | Val | Gly | Asp | Arg | Val | Thr – "CDR Grafted" VL |
| * |  | * |  | * |  |  |  |
| Val | Ser | Leu | Gly | Glu | Arg | Val | Thr – Murine 1308F VL |

|  |  | 35 |  |  |  | 40 |  |
|---|---|---|---|---|---|---|---|
| Leu | Ala | Trp | Tyr | Gln | Gln | Lys | Pro |
|  | * |  |  |  |  |  |  |
| Leu | Asn | Trp | Tyr | Gln | Gln | Lys | Pro |
|  |  |  | * |  |  |  |  |
| Leu | Asn | Trp | Phe | Gln | Gln | Lys | Pro |

|  |  | 55 |  |  |  | 60 |  |
|---|---|---|---|---|---|---|---|
| Ser | Leu | Glu | Ser | Gly | Val | Pro | Ser |
| * |  | * | * |  |  |  |  |
| Arg | Leu | Val | Asp | Gly | Val | Pro | Ser |
| CDR 2 |  |  |  |  |  |  |  |
| Arg | Leu | Val | Asp | Gly | Val | Pro | Ser |

|  |  | 75 |  |  |  | 80 |  |
|---|---|---|---|---|---|---|---|
| Leu | Thr | Ile | Ser | Ser | Leu | Gln | Pro |
| Leu | Thr | Ile | Ser | Ser | Leu | Gln | Pro |
|  |  |  |  |  |  |  | * |
| Leu | Thr | Ile | Ser | Ser | Leu | Glu | Phe |

|  |  | 95 |  |  | 100 |  |  |
|---|---|---|---|---|---|---|---|
| Ser | Tyr | Ser | – | – | – |  |  |
| * | * | * |  |  |  |  |  |
| Glu | Phe | Pro | Tyr | Thr | Phe | Gly | Gly |
| CDR 3 |  |  |  |  |  |  |  |
| Glu | Phe | Pro | Tyr | Thr | Phe | Gly | Gly |
|  |  | <<V / J>> |  |  |  |  |  |

FIG. 3A

```
5'  gcgaattccatggactgacctggagggtc 3'
        MetAspTrpThrTrpArgValPheCysLeuLeuAlaValAlaAlaProGlyAlaHisSerGln
5'    ccATGGACTGGACCTGGAGGGTCTTCTGCTTGCTGGCTGTAGCACCAGGTGCCCACTGCCAG
       1---------+---------+---------+---------+---------+---------+
3'      TACCTGACCTGGACCTCCCAGAAGACGAACGACCGACATCGTGGTCCACGGGTGAGGGTC ValGlnLeuValGlnSerGlyAlaGluValLysLysProGlyAlaSerValLysValSer
      GTGCAGTGGTGCAGTCTGGAGCTGAGGTGAAGAAGCCTGGAGCCTCAGTGAAGGTTTCC
     61---------+---------+---------+---------+---------+---------+
      CACGTCGACCACGTCAGACCTCGACTCCACTTCTTCGGACCTCGGAGTCACTTCCAAAGG CysLysAlaSerGlyPheAsnIleLysAspTyrTyrIleTyrTrpValArgGlnAlaPro
      TGCAAGGCATCTGGATTCAACATTAAGGACTACTACATTTACTGGGTGCGACAGGCTCCT
     121---------+---------+---------+---------+---------+---------+
      ACGTTCCGTAGACCTAAGTTGTAATTCCTGATGATGTAAATGACCCACGCTGTCCGAGGA GlyGlnGlyLeuGluTrpMetGlyTrpIleAspProGluAsnGlyAsnThrValPheAsp
      GGACAAGGGCTCGAGTGGATGGGTTGGATTGACCCTGAGAATGGTAATACTGTGTTTGAC
     181---------+---------+---------+---------+---------+---------+
      CCTGTTCCCGAGCTCACCTACCCAACCTAACCTGGACTCTTACCATTATGACACAAACTG
```

FIG. 3B

```
     ProLysPheGlnGlyArgValThrThrArgAspThrSerThrSerThrValTyrMet
     CCGAAGTTCCAGGGCAGAGTCACCATGACCAGGGACACGTCCACGAGCACAGTCTACATG
241  ------+---------+---------+---------+---------+---------+
     GGCTTCAAGGTCCCGTCTCAGTGGTACTGGTCCCTGTGCAGGTGCTCGTGTCAGATGTAC

GluLeuSerSerLeuArgSerGluAspThrAlaValTyrTyrCysAlaTyrTyrGlyThr
     GAGCTGAGCAGCCTGAGATCTGAGGACACGGCCGTGTATTACTGTGCGTACTACGGTACA
301  ------+---------+---------+---------+---------+---------+
     CTCGACTCGTCGGACTCTAGACTCCTGTGCCGGCACATAATGACACGCATGATGCCATGT

SerSerPheAspPheTrpGlyGlnGlyThrThrLeuThrValSerSer
     AGCTCCTTTGACTTCTGGGGCCAAGGCACCACTCTCACAGTGAGCTCA
361  ------+---------+---------+---------+---------+

TCGAGGAAACTGAAGACCCCGGTTCCGTGGTGAGAGTGTCACTCGAGTattcctagg   5'
                                                              3'
      ggtgagagtgtcactcgagtattcctagggc   5'
```

FIG. 4A

```
cgcggatccatggacatgagggtcccc
         MetAspMepArgValProAlaGlnLeuLeuLeuGlyLeuLeuLeuTrpLeuProGlyAla
      ccATGGACATGAGGGTCCCCGCTCCAGCTCCTGCTCCTGGGCCTCCTGCTCTGGCTCCCAGGTGCC
   1  ----+----|----+----|----+----|----+----|----+----|----+----|----
      TACCTGTACTCCCAGGGGCGAGTCGAGGTCGAGGACGAGGACGAGACCGAGGGTCCACGG LysCysAspIleGlnMetThrGlnSerProSerThrLeuSerAlaSerValGlyAspArg
      AAATGTGATATCCAGATGACCCAGTCTCCTTCCACCCTGTCTGCATCTGTAGGAGACAGA
  61  ----+----|----+----|----+----|----+----|----+----|----+----|----
      TTTACACTATAGGTCTACTGGGTCAGAGGAAGGTGGGACAGAGACGTAGACATCCTCTGTCT ValThrIleThrCysLysAlaSerGlnAspIleAsnArgTyrLeuAsnTrpTyrGlnGln
      GTCACCATCACTTGCAAGGCCAGTCAGGACATTAATAGGTAGTTAAACTGGTACCAGCAG
 121  ----+----|----+----|----+----|----+----|----+----|----+----|----
      CAGTGGTAGTGAACGTTCCGGTCAGTCCTGTAATTATCCATCAATTTGACCATGGTCGTC LysProGlyLysAlaProLysLeuLeuIleTyrArgAlaAsnArgLeuValAspGlyVal
      AAACCCGGGAAAGCCCTAAGCTCCTGATCTATCGTGCAAACAGATTGGTAGATGGGGTC
 181  ----+----|----+----|----+----|----+----|----+----|----+----|----
      TTTGGGCCCTTTCGGGATTCGAGGACTAGATAGCACGTTTGTCTAACCATCTACCCCAG
```

FIG. 4B

```
      ProSerArgPheSerGlySerGlyThrGlyGluPheThrLeuThrIleSerSerLeu
      CCATCAAGGTTCAGCGGCGGCAGTGGGATCTGGGACAGAATTCACTCTCCACCATCAGCAGCCTG
241   ----+----|----+----|----+----|----+----|----+----|----+----|
      GGTAGTTCCAAGTCGCCGCCGTCACCCTAGACCCTGTCTTAAGTGAGAGTGTTAGTCGTCGGAC

GlnProAspAspPheAlaThrTyrTyrCysLeuGlnPheHisGluPheProTyrThrPhe
      CAGCCTGATGATTTTGCAACTTATTACTGCCTACAGTTTCATGAGTTTCCGTACACGTTC
301   ----+----|----+----|----+----|----+----|----+----|----+----|
      GTCGGACTACTAAAACGTTGAATAATGACGGATGTCAAAGTACTCAAAGGCATGTGCAAG
                                                              3' gtgcaag GlyGlyGlyThrLysLeuGluIleLys
      GGAGGGGGACCAAGCTTGAAATAAAA 3'
361   ----+----|----+----|
      CCTCCCCCCTGGTTCGAACTTTATTTT 5'
      cctcccccctggttcgaaccc 5'
```

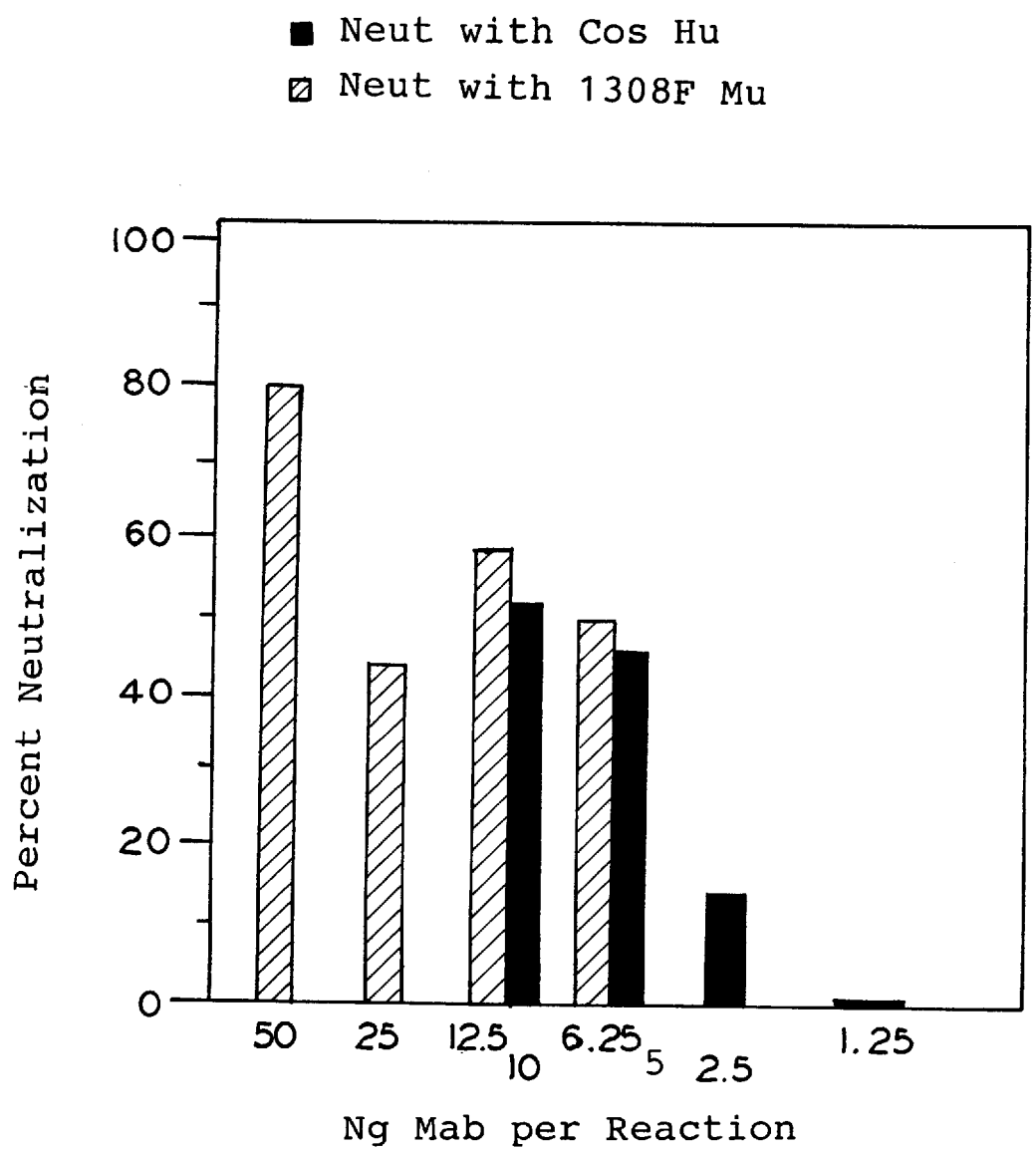

FIG. 7A

```
             1               5                  10                 15
    1   Gln Val Thr Leu Arg Glu Ser Gly Pro Ala Leu Val Lys Pro Thr    Human VH (Cor)
        Gln Val Thr Leu Arg Glu Ser Gly Pro Ala Leu Val Lys Pro Thr    "Humanized" VH
                    *                           *   *
        Gln Val Glu Leu Gln Glu Ser Gly Pro Gly Ile Leu Gln Pro Ser    Murine 1129 VH 16   Gln Thr Leu Thr Leu Thr Cys Thr Phe Ser Gly Phe Ser Leu Ser
        Gln Thr Leu Thr Leu Thr Cys Thr Phe Ser Gly Phe Ser Leu Ser
        Gln Thr Leu Ser Leu Thr Cys Ser Phe Ser Gly Phe Ser Leu Ser 31   Ser Ser Gly Met Cys Val Gly Trp Ile Arg Gln Pro Pro Gly Lys
                    *
        Thr Ser Gly Met Ser Val Gly Trp Ile Arg Gln Pro Pro Gly Lys
                                                            *
        Thr Ser Gly Met Ser Val Gly Trp Ile Arg Gln Pro Ser Gly Glu 46   Ala Leu Glu Trp Leu Ala Asp Ile Trp Asp Asp Asp Lys Lys Asp
        Ala Leu Glu Trp Leu Ala Asp Ile Trp Asp Asp Asp Lys Lys Asp
            *                           *
        Gly Leu Glu Trp Leu Ala Asp Ile Trp Trp Asp Asp Lys Lys Asp
```

FIG. 7B

```
 61  Tyr Asn Thr Ser Leu Asp Thr Arg Leu Thr Ile Ser Lys Asp Thr
                          *
     Tyr Asn Pro Ser Leu Lys Ser Arg Leu Thr Ile Ser Lys Asp Thr
     Tyr Asn Pro Ser Leu Lys Ser Arg Leu Thr Ile Ser Lys Asp Thr
     Swe Lys Asn Gln Val Val Leu Thr Val Thr Asn Met Asp Pro Ala
                                      *
 76  Ser Lys Asn Gln Val Val Leu Lys Val Thr Asn Met Asp Pro Ala
                              *                           *
     Ser Ser Asn Gln Val Phe Leu Lys Ile Thr Gly Val Asp Thr Ala
     Asp Thr Ala Thr Tyr Tyr Cys Ala Arg Ile Yhr Val Ile Pro Ala Pro Ala Gly
                                              *       *   *
 91  Asp Thr Ala Thr Tyr Tyr Cys Ala Arg Ser Met Ile Thr Asn Trp
                                          *       *
     Asp Thr Ala Thr Tyr Tyr Cys Ala Arg Ser Met Ile Thr Asn Trp
     Tyr Met Asp Val Trp Gly Arg Gly Thr Pro Val Thr Val Ser Ser
         *                       *
106  Tyr Phe Asp Val Trp Gly Ala Gly Thr Thr Val Thr Val Ser Ser
                                          *
     Tyr Phe Asp Val Trp Gly Ala Gly Thr Thr Val Thr Val Ser Ser
```

FIG. 8A

```
                  5                   10                  15
Asp Ile Gln Met Thr Gln Ser Pro Ser Thr Leu Ser Ala Ser Val    — Human K102 VL
                                                                  (SEQ ID 33)
Asp Ile Gln Met Thr Gln Ser Pro Ser Thr Leu Ser Ala Ser Val    — "CDR Grafted" VL
  *                                                               (SEQ ID 34)
Asp Ile Gln Leu Thr Gln Ser Pro Ala Ile Met Ser Ala Ser Pro    — Murine 1129 VL
                                                                  (SEQ ID 35)

20                  25                  30
Gly Asp Arg Val Thr Ile Thr Cys Arg Ala Ser Gln Ser Ile Ser
Gly Asp Arg Val Thr Ile Thr Cys Lys Cys Gln Leu Ser Val Gly
  *                                   *   *   *   *   *   *
                                          ────────CDR 1───────
Gly Glu Lys Val Thr Met Thr Cys Lys Cys Ser Ser Val Gly 35                  40                  45
Ser Trp Leu Ala Trp Tyr Gln Gln Lys Pro Gly Lys Ala Pro Lys
  *
Tyr Met His  —   Trp Tyr Gln Gln Lys Pro Gly Lys Ala Pro Lys
──────────
Tyr Met His  —   Trp Tyr Gln Gln Lys Ser Ser Thr Ser Pro Lys 50                  55                  60
Leu Leu Ile Tyr Asp Ala Ser Ser Leu Glu Ser Gly Val Pro Ser
Leu Trp Ile Tyr Asp Thr Ser Lys Leu Ala Ser Gly Val Pro Ser
                ─────────CDR 2──────────             *
Leu Trp Ile Tyr Asp Thr Ser Lys Leu Ala Ser Gly Val Pro Gly
```

FIG. 8B

```
                65              70              75
Arg Phe Ser Gly Ser Gly Ser Gly Thr Glu Phe Thr Leu Thr Ile
Arg Phe Ser Gly Ser Gly Ser Gly Thr Glu Phe Thr Leu Thr Ile
                                  *   *
Arg Phe Ser Gly Ser Gly Ser Gly Asn Ser Tyr Ser Leu Thr Ile
                80              85              90
Ser Ser Leu Gln Pro Asp Asp Phe Ala Thr Tyr Tyr Cys Gln Gln
Ser Ser Leu Gln Pro Asp Asp Phe Ala Thr Tyr Tyr Cys Gln Gln
                      *
Ser Ser Ile Gln Ala Glu Asp Val Ala Thr Tyr Tyr Cys Phe Gln
                95              100             105
Tyr Asn Ser Tyr Ser
 *       *
Gly Ser Gly Tyr Pro Phe Thr Phe Gly Gly Gly Thr Lys Leu Glu Ile Lys
        CDR 3
Gly Ser Gly Tyr Pro Phe Thr Phe Gly Gly Gly Thr Lys Leu Glu Ile Lys

```
SJ153  5'-GGCGTCGACTCACC-
           ATGGACTGGACCTGGAGGGTCTTCTGCTTGCTGTAGCACCAGGTGCCACTCCC-3'
                                                  SJ150 5'-CCAG
    1    ----+----+----+----+----+----+                         60
         MetAspTrpThrTrpArgValPheCysLeuLeuAlaValAlaProGlyAlaHisSerGln

GTCACCTTAAGGGAGTCTGGTCCCTGGCCCCTGAAACCCACAGACCCTCACACTGACC
   61    ----+----+----+----+----+----+                        120
                                        3'-GGAGTGTGACTGG
         ValThrLeuArgGluSerGlyProAlaLeuValLysProThrGlnThrLeuThr

TGCACC-3'                               SJ151 5'- CAG
         ACGTGGAAGAGACCCAAAAAGTGACTCGTGAAGACCATACTCACATCCGACCTAAGCAGTC
  121    ----+----+----+----+----+----+                        180
         CysThrPheSerLeuSerThrGlyMetSerValGlyTrpIleArgGln

CCCCCAGGGAAGGCCCTGCACTCGCTTGCAGACATTTGGTGGGATGACAAAAGGACTAT
  181    ----+----+----+----+----+----+                        240
         GGGGGTCCCTTCCGGG-5' SJ149                        3'- GATA
         ProProGlyLysAlaLeuGluTrpLeuAlaAspIleTrpTrpAspAspLysLysAspTyr
```

FIG. 9B

```
                                                              SJ152 5'-GGTC
     AATCCATCCCTGAAG-3'                                                  300
241  ---------+---------+---------+---------+---------+---------+
     TTAGGTACCGACTTCTCGGCCGAGTGTTAGAGGTTCCTATGGAGGTTTTTGGTCCACCAG
     AsnProSerLeuLysSerArgLeuThrIleGerLysAspThrSerLysAsnGlnValVal

CTTAAAGTGACCAACATGGACTCCTGCTGATACTGCCACTTACTACTGTGCTCGGTCTATG       360
301  ---------+---------+---------+---------+---------+---------+
     GAATTTCACTGGTTG-5' SJ148                                 3'-TAC
     LeuLysValThrAsnMetAspProAlaAspThrAlaThrTyrTyrCysAlaArgSerMet 417
361  ---------+---------+---------+---------+---------+-----
     TAGTGCTTGACCATGAAGCTACAGACCCCGCCCTGGTGCCAGTGGCACTCGAGTCCG-5' SJ147
     IleThrAsnTrpTyrPheAspValTrpGlyAlaGlyThrThrValSerSer
```

5,824,307

HUMAN-MURINE CHIMERIC ANTIBODIES AGAINST RESPIRATORY SYNCYTIAL VIRUS

This application is a continuation-in-part of U.S. application Ser. No. 07/813,372, filed on Dec. 23, 1991, now abandoned.

BACKGROUND

Respiratory syncytial virus (RSV) is the major cause of acute respiratory illness in young children admitted to hospitals, and the community practice will treat perhaps five times the number of hospitalized children. It is therefore, the most common cause of lower respiratory tract infection in young children. While the majority of community-acquired RSV infections resolve themselves in a week to ten days, many hospitalized children, especially under six months of age require assisted ventilation.

Efforts to produce an effective vaccine have been unsuccessful (8). A major obstacle to vaccine development is safety; the initial formalin inactivated RSV vaccine caused an increased incidence of RSV lower respiratory tract disease and death in immunized children upon exposure to virus (5).

Recently, the drug ribavirin has been licensed for therapy of RSV pneumonia and bronchiolitis (2,3); its value is controversial (4). Although ribavirin has shown efficacy (9), the drug has to be administered over an 18 hour period by aerosol inhalation. In addition, the level of secondary infections following cessation of treatment is significantly higher than in untreated patients.

Studies have shown that high-titered RSV immunoglobulin was effective both in prophylaxis and therapy for RSV infections in animal models (6, 7). Infected animals treated with RSV immune globulin, showed no evidence of pulmonary immune-complex disease (6, 7).

Even if RSV hyperimmune globulin is shown to reduce the incidence and severity of RSV lower respiratory tract infection in high risk children, several disadvantages may limit its use. One drawback is the necessity for intravenous infusion in these children who have limited venous access because of prior intensive therapy. A second disadvantage is the large volume of RSVIG required for protection, particularly since most these children have compromised cardiopulmonary function. A third disadvantage is that intravenous infusion necessitates monthly hospital visits during the RSV season which places these children at risk of nosocomial RSV infection (1). A final problem is that it may prove to be very difficult to select sufficient donors to produce a hyperimmune globulin for RSV to meet the demand for this product. Currently only about 8% of normal donors have RSV neutralizing antibody titers high enough to qualify for the production of hyperimmune globulin.

Another approach may be the development of monoclonal antibodies with high specific neutralizing activity as an alternative to hyperimmune globulin. It is preferable, if not necessary, to use human monoclonal antibodies rather than murine or rat antibodies to minimize the development of human anti-rodent antibody responses which may compromise the therapeutic efficacy of the antibody or induce immune-complex pathology. However, the generation of human monoclonal antibodies with the desired specificity may be difficult and the level of production from human cell lines is often low, precluding their development.

An alternative approach involves the production of human-mouse chimeric antibodies in which the genetic information encoding the murine heavy and light chain variable regions are fixed to genes encoding the human heavy and light constant regions. The resulting mouse-human hybrid has about 30% of the intact immunoglobulin derived from murine sequences. Therefore, although a number of laboratories have constructed chimeric antibodies with mouse variable and human constant domains (10–18), the mouse variable region may still be seen as foreign (19).

SUMMARY OF THE INVENTION

It is therefore an object of the present invention to provide a complementarity determining region (CDR)-grafted human antibody which contains at least one CDR from each variable heavy chain and variable light chain of at least one monoclonal antibody, against the RSV antigen. The monoclonal antibody may be derived from any non-human animal, preferably however, it is derived from a rodent and most preferably it is a murine monoclonal antibody. Preferably, the murine monoclonal antibody is a neutralizing antibody. It is also preferable that said murine antibody is an antibody against RSV F antigen.

The term "animal" as used herein is used in its broadest sense includes mammals including humans.

DETAILED DESCRIPTION OF THE DRAWINGS

The drawings depicted and described herein are intended to further illustrate the present invention and are not intended to limit the invention in any manner whatsoever.

FIG. 1 shows the amino acid (AA) sequence design of CDR-Grafted anti-RSV F glycoprotein $V_H$. The figure depicts the AA sequence for the human HV3 $V_H$ before grafting (SEQ ID NO:16), CDR grafted $V_H$ (SEQ ID NO:17), and murine MAb1308F $V_H$ (SEQ ID NO:18) from which the CDR sequence was grafted. The heavily underlined regions identify the CDR sequence which was grafted into the human HV3 $V_H$ and each of the three regions is identified as CDR1, CDR2 and CDR3, respectively.

FIG. 2 shows the amino acid (AA) sequence design of CDR-Grafted anti-RSV F Protein $V_L$. The figure depicts the AA sequence for the human K102 $V_L$ before grafting (SEQ ID NO:19), CDR grafted $V_L$ (SEQ ID NO:20), and murine MAb1308F $V_L$ (SEQ ID NO:21) from which the CDR sequence was grafted. The heavily underlined regions identify the CDR sequence which was grafted into the human K102 $V_L$ and each of the three regions is identified as CDR1, CDR2 and CDR3, respectively.

FIG. 3 depicts the oligonucleotides used to make Hu1308$V_H$, the sequences which are underlined are the specific primer sequences (SEQ ID NO:22–25).

FIG. 4 depicts the oligonucleotides used to make Hu1308$V_L$, the sequences which are underlined are the specific primer sequences (SEQ ID NO:26–29).

FIG. 6 depicts a graph of the Neutraliziation of RSV as percent neutralization versus ng MAb per reaction for neutralizing with Cos Hu1308F and with Mu1308F.

FIG. 7 shows the amino acid (AA) sequence design of CDR-Grafted anti-RSV F glycoprotein $V_H$. The figure depicts the AA sequence for the human COR $V_H$ before grafting (SEQ ID NO:30), CDR grafted $V_H$ (SEQ ID NO:31), and murine MAb1129 $V_H$ (SEQ ID NO:32) from which the CDR sequence was grafted. The heavily underlined regions identify the CDR sequence which was grafted into the human COR $V_H$ and each of the three regions is identified as CDR1, CDR2 and CDR3, respectively.

FIG. 8 shows the amino acid (AA) sequence design of CDR-Grafted anti-RSV F Protein $V_L$. The figure depicts the AA sequence for the human K102 $V_L$ before grafting (SEQ ID NO:33), CDR grafted $V_L$ (SEQ ID NO:34), and murine MAb1129 $V_L$ (SEQ ID NO:35) from which the CDR sequence was grafted. The heavily underlined regions identify the CDR sequence which was grafted into the human K102 $V_L$ and each of the three regions is identified as CDR1, CDR2 and CDR3,respectively.

FIG. 9 shows the oligonucleotides used to construct the humanized 1129 V (SEQ ID NO:36–42).

Figure 10:
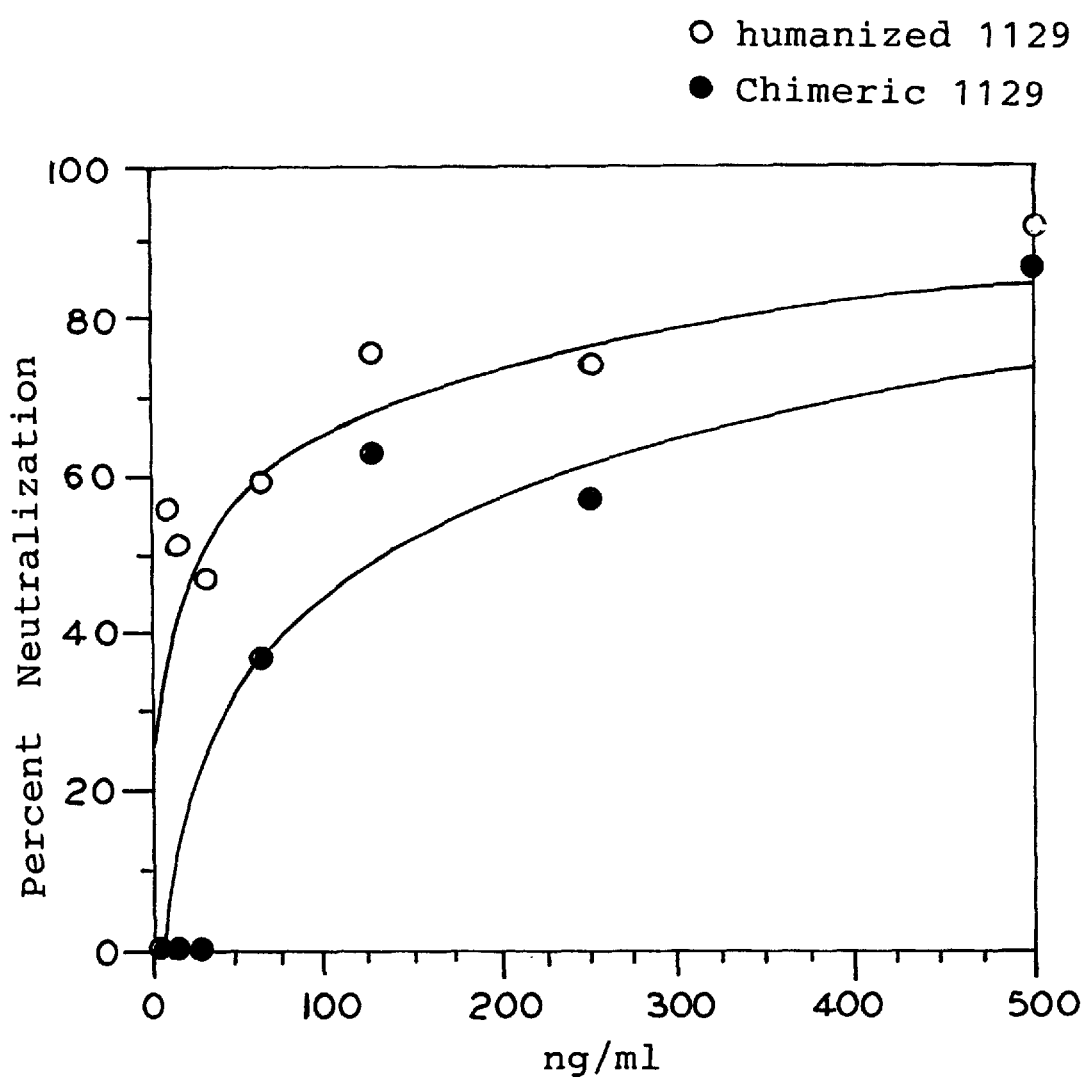

FIG. 10 shows binding data for humanized 1129 in an ELISA assay.

DETAILED DESCRIPTION OF THE INVENTION

Applicants have found that transplantation into a human antibody, of only the genetic information for at least one CDR from each of the variable heavy and variable light chain derived from murine monoclonal antibody against RSV antigen, is effective for the prevention and treatment of RSV in animals. Preferably the murine antibody is a neutralizing antibody against RSV. Another aspect of the present invention provides for the murine antibody to be an antibody against RSV F antigen. Preferably, the murine antibody is neutralizing antibody against RSV F antigen. The substitution of the mouse CDR's into the human variable framework segments minimizes the potential for human anti-mouse antibody (HAMA) responses while retaining binding affinity and specificity for antigen, RSV F protein. Since, the CDR's do not contain characteristic murine or human motifs, the human antibodies containing the murine antibody CDR's are essentially indistinguishable from completely human antibodies, thereby, minimizing the human antibody response while retaining binding affinity and specificity for RSV F antigen.

The development of a humanized antibody against RSV F antigen began with a murine antibody against RSV F antigen. Examples of murine antibodies of this type are: MAb 1436C, MAb 113, MAb 112, MAb 151, MAb 1200, MAb 1214, MAb 1237, MAb 1129, MAb 1121, MAb 1107, MAb 131-1, MAb 43-1, MAb 1112, MAb 1269, MAb 1243, MAb 1331H, MAb 1308F and MAb 1302A (see citation 21).

An aspect of the present invention provides that the CDRs of the human antibody are comprised of three complementarity determining regions (CDRs) from each variable heavy and variable light chain of the murine antibody.

The murine antibodies against RSV F antigen have been mapped by competitive binding and reactivity profiles of virus escape mutants to three broad antigenic sites (A, B, C) containing 16 distinct epitopes (20). The epitopes within antigenic sites A and C have shown the least variability in natural isolates.

Therefore, another aspect of this invention provides for a human antibody containing at least one CDR from each variable heavy and variable light chain of at least one murine antibody against RSV F antigen which is specific for antigenic site A or C. In one aspect, this invention provides for the murine antibody against RSV F antigen specific for antigenic site C, where the murine antibody is MAb 1308F.

In such an embodiment of this invention a human antibody contains CDR's of the variable heavy chain of murine antibody MAb 1308F against the RSV F antigen. The CDR variable heavy chain of MAb 1308F comprises three CDRs having the following amino acid sequences: Nos. 31 to 35, 47 to 60 and 99 to 106. In addition, this embodiment contains CDR's of a variable light chain of MAb 1308F of murine antibody against RSV F antigen. The CDR variable light chain comprises three CDR's having the following amino acid sequences: Nos. 24 to 34, 50 to 56 and 89 to 97.

Another aspect of this invention provides for a human antibody containing at least one CDR from each variable heavy and variable light chain of at least one murine antibody against RSV F antigen which is specific for antigenic site C. Preferably, this invention provides for the murine antibody against RSV F antigen specific for antigenic site C, where the murine antibody is MAb 1129.

In the embodiment of this invention a human antibody which contains CDR's of the variable heavy chain of murine antibody MAb 1129 against the RSV F antigen. The CDR variable heavy chain of MAb 1129 comprises three CDRs having the following amino acid sequences: Nos. 31 to 36, 52 to 67 and 100 to 109. In addition, this embodiment contains CDR's of a variable light chain of MAb 1129 of murine antibody against RSV F antigen. The CDR variable light chain comprises three CDR's having the following amino acid sequences: Nos. 24 to 33, 51 to 56 and 89 to 96.

An additional aspect of applicants' invention is a process for preventing or treating RSV infection comprising administering to the animal an effective amount of a human antibody containing at least one CDR from each variable heavy and variable light chain, of at least one murine antibody against RSV F antigen.

Another aspect of applicants' invention is a composition comprising administering an effective amount of the human antibody as described above in conjunction with an acceptable pharmaceutical carrier. Acceptable pharmaceutical carriers include but are not limited to non-toxic buffers, fillers, isotonic solutions, etc.

The composition of Applicant's invention may be administered topically or systemically. Examples of topical administration are intranasal administration and inhalation of an aerosol containing the human antibody composition. Systemic administration may be accomplished by intravenous or intramuscular injection of the human antibody composition.

A preferred aspect of Applicants' invention is that the human antibody is administered as part of a plurality of human antibodies against RSV F antigen. These antibodies can be against the same or different epitopes of the RSV F antigen.

Additionally, the human antibody of this invention can be used clinically for diagnosing respiratory syncytial virus in patients. Because of their affinity for RSV F antigen these human antibodies can be used in known diagnostic assay procedures for detecting the presence and concentration of RSV F antigen cells in samples, e.g., body fluids. The human antibodies of the present invention can for example be attached or bound to a solid support, such as latex beads, a column, etc., which are then contacted with a sample believed to contain RSV F antigen.

Applicants' development of human antibodies against RSV, began with murine hybridoma cells producing murine monoclonal antibodies which have been shown to neutralize RSV in vitro and protect cotton rats against lower respiratory tract infection with RSV.

One such antibody was selected, which is specific for antigenic site C, to produce mouse-human chimeric antibodies. This antibody was chosen on the basis that it: (i) reacted with a large number of virus strains tested (at least 13 out of 14 isolated); (ii) retained neutralizing activity against virus escape mutants selected with other anti-F antibodies and (iii) blocked RSV replication when administered at low doses to cotton rats by intranasal route prior to virus challenge. The antibody showed significant reduction in pulmonary virus titer among antibodies in that respective region. Murine antibody 1308F, specific for the C region of RSV F protein, was chosen as the initial target for humanization.

In summary, the human antibodies were constructed as follows: the RNA was extracted from the murine antibody-producing cell line, the murine variable regions which are responsible for the binding of the antibody to RSV were cloned and sequenced, resulting in the identification of the murine antibody CDRs. Then a human variable heavy and light chain framework sequence having the highest homology with the variable heavy and light chain murine antibody, was selected. A human framework sequence such as described above is best able to accept the murine-derived CDRs.

The murine 1308F variable heavy chain was compared to various human germline genes, the highest homology was to the human germline gene HV3. The two sequences were 62% homologous overall and 65% in the framework regions. Significantly, there is good homology at the junctions of the CDR segments and the frameworks with the exception of the 5' end of FR2. The murine derived variable heavy chain CDRs were then substituted into the variable heavy chain human germline gene HV3. The mouse and human sequences as well as that of a potential CDR-Grafted combination of the two is shown in FIG. 1.

A similar analysis of the $V_L$ region revealed high homology to the human germ line V-Kappa gene K 102. The alignment of these sequences is shown in FIG. 2. In this case the homology is 62% overall and 73% in the framework regions. The murine-derived variable light CDRs were then substituted into the human variable light chain of human germline gene K102. In each case a human J-region can be selected which is identical to the mouse sequence.

In another embodiment, murine 1129 variable heavy chain was compared to various human variable region amino acid sequences, the highest homology was to the human rearranged COR sequence. The two amino acid sequences were 75% homologous overall and 80% in the framework regions. Significantly, there is good homology at the junctions of the CDR segments and the frameworks. The murine derived variable heavy chain CDRs were then substituted into the variable heavy chain human COR $V_H$ sequence. The mouse and human sequences as well as that of a potential CDR-Grafted combination of the two is shown in FIG. 1.

A similar analysis of the $V_L$ region revealed high homology to the human germ line K102. The alignment of these sequences is shown in FIG. 8. In this case the homology is 73% overall and 82% in the framework regions. The murine-derived variable light CDRs were then substituted into the human variable light chain of human germline K102. In this case a human J-region, human JK4, was selected which is similar to the mouse sequence.

Therefore, human antibodies are expressed and characterized relative to the parental murine antibodies to be certain that the genetic manipulation has not drastically altered the binding properties of the antibodies.

Applicants present herein examples which are further illustrative of the claimed invention but not intended to limit the invention.

EXAMPLE 1
cDNA cloning and sequencing of anti-RSV F Protein antibody 1308F cDNA copies of the $V_H$ and $V_L$ of the target antibody were generated as follows. The first strand cDNA reaction was carried out using AMV reverse trenscriptase and a phosphorylated oligonucleotide primer complementary to a segment of the mRNA coding for the constant region of the particular heavy or light chain isotype. For 1308F the isotype is gammal, kappa and the specific oligonucleotides were 5'AGCGGATCCAGGGGCCAGTGGATAGAC (SEQ ID NO:1) complementary to codons 129–137 of the CH1 region of the murine Gammal gene, and 5'TGGATGGTGGGAA-GATG (SEQ ID NO:2) complementary to codons 116–122 of the murine C-kappa gene. The primer anneals to a segment of the mRNA adjacent to the variable region. Second strand cDNA synthesis was carried out using RNase H and E. coli DNA polymerase I, as described by Gubler and Hoffman (Gene 25,;263, 1983), followed by T4 DNA polymerase to assure that blunt ends are produced.

| Signal | V | J | C | mRNA |
|---|---|---|---|---|
|  | 1st strand | cDNA |  |  |
|  | 2nd strand | cDNA |  |  |

The ds-cDNA was ligated into pUC18 which had been digested with restriction endonuclease SmaI and treated with alkaline phosphatase. The ligation was used to transform E. coli DH5a by the method of Hanahan (J. Mol. Biol. 166;557, 1983). Oligonucleotide probes corresponding to C-region sequence lying between the first strand cDNA primer and the V-region were used in colony hybridizations to identify transformants carrying the desired cDNA segment. The specific probe sequences were GGCCAGTGGATAGAC (SEQ ID NO:3) complementary to codons 121–125 of murine CH1 regions and TACAGTTGGTGCAGCA (SEQ ID NO:4) complementary to codons 110–115 of c-Kappa, respectively. Candidate plasmids, isolated from colonies which were positive in the hybridization, were analyzed by digestion with restriction endonucleases Eco RI and Hind III to release the CDNA insert. Those with inserts of 400–500 bp were subjected to DNA sequencing.

The cDNA inserts were inserted into M13 mp18 and mp19 for the determination of the DNA sequence on both strands. Single stranded DNA from the resulting recombinant bacteriophage was isolated and sequenced by the dideoxy chain termination method (Proc. Nat. Acad. Sci. USA 74; 5463, 1977).

In order to confirm that the pair of rearranged and somatically mutated V gene cDNA's isolated from the 1308F hybridoma represented those which were in the 1308F antibody, a single-chain Fv gene was generated, expressed in and secreted from mammalian cells, then assayed for binding to RS virus. Competition binding experiments then were used to demonstrate the identity of the binding site.

EXAMPLE 2
Design and assembly of human 1308F $V_H$ and $V_L$

The CDR regions of the $V_H$ and $V_L$ were identified by comparing the amino acid sequence to known sequences as described by Kabat (38). In order to select the human framework sequences best able to accept the mouse derived CDR sequences in a conformation which retains the structure of the antigen combining site, the following strategy was employed. First, the sequence of the murine $V_H$ and $V_L$ regions will be compared to known human sequences from both the Genbank and NBRF protein databanks using the Wordsearch program in the Wisconsin package of sequence manipulation programs (Nucleic Acid Res. 12; 387). The best several human V-regions were then analyzed further on the basis of similarity in the framework regions, especially at the junctions of the framework and CDR regions (see FIGS. 1 and 2).

The CDR-grafted $V_H$ region together with the respective leader sequence of the human v-region gene was synthesized de novo using four overlapping oligonucleotides ranging from 100–137 nucleotides in length (see FIG. 3). The oligonucleotides were first allowed to anneal in pairwise combinations and extended with DNA polymerase to generate approximately 200 bp ds DNA fragments with an overlapping region. the fragments were then mixed and subjected to PCR using primers at the 3' end of one fragment and the 5' end of the other fragment. The only product which can be formed under these condition is the full length $V_H$ segment. The specific primer sequences are underlined in FIG. 3. An endonuclease Sac I site was included at the 3' end of the $V_H$ sequence in order to join it to a human constant region gene segment.

The CDR-grafted $V_L$ region was synthesized in a similar way (see FIG. 4). In this instance the initial 200 bp fragments were amplified separately and inserted into separate plasmeds. The fragment coding for the amino terminus was cloned into a pUC18 derivative as an NcoI-SmaI fragment while the fragment coding for the carboxyl-terminus was cloned as a SmaI to Hind III fragment. The fragments were subsequently combined via a SmaI site at the junction. The oligonucleotides are indicated in FIG. 4. A Hind III site was included near the 3' end of the gene segment in order to join it to a human C-kappa gene.

EXAMPLE 3
Construction of Vectors for 1308F expression

The NcoI-SacI fragment representing the humanized $V_H$ was joined to a SacI-NotI fragment representing a human c-Gamma I CDNA and inserted into pS 18 (which is pUC 18 with NcoI and NotI restriction sites incorporated into the polylinker region between the BamHI and KpnI sites). The humanized 1308F-gammaI gene on a SacI-NotI fragment was then combined with a PvuI-NotI fragment from pSJ37 carrying a poly A addition site and a PvuI-SacI fragment from pSV2-dhfr-pCMV containing the SV40 origin of replication, a dhfr gene and the CMV immediate early promoter. The resulting plasmid was designated pSJ60.

The NcoI-HindIII fragment representing the humanized $V_L$ was joined to a HindIII-NotI fragment representing a human c-Kappa CDNA in pS18. The humanized 1308F-Kappa gene on a SalI-NotI fragment was then combined with a PvuI-NotI fragment from pSJ37 carrying a poly A addition site and a PvuI-SalI fragment from pSV2-dhfr-pCMV, containing the SV40 origin of replication, a dhfr gene and the CMV immediate early promoter. The resulting plasmid was designated pSJ61.

Figure 5:
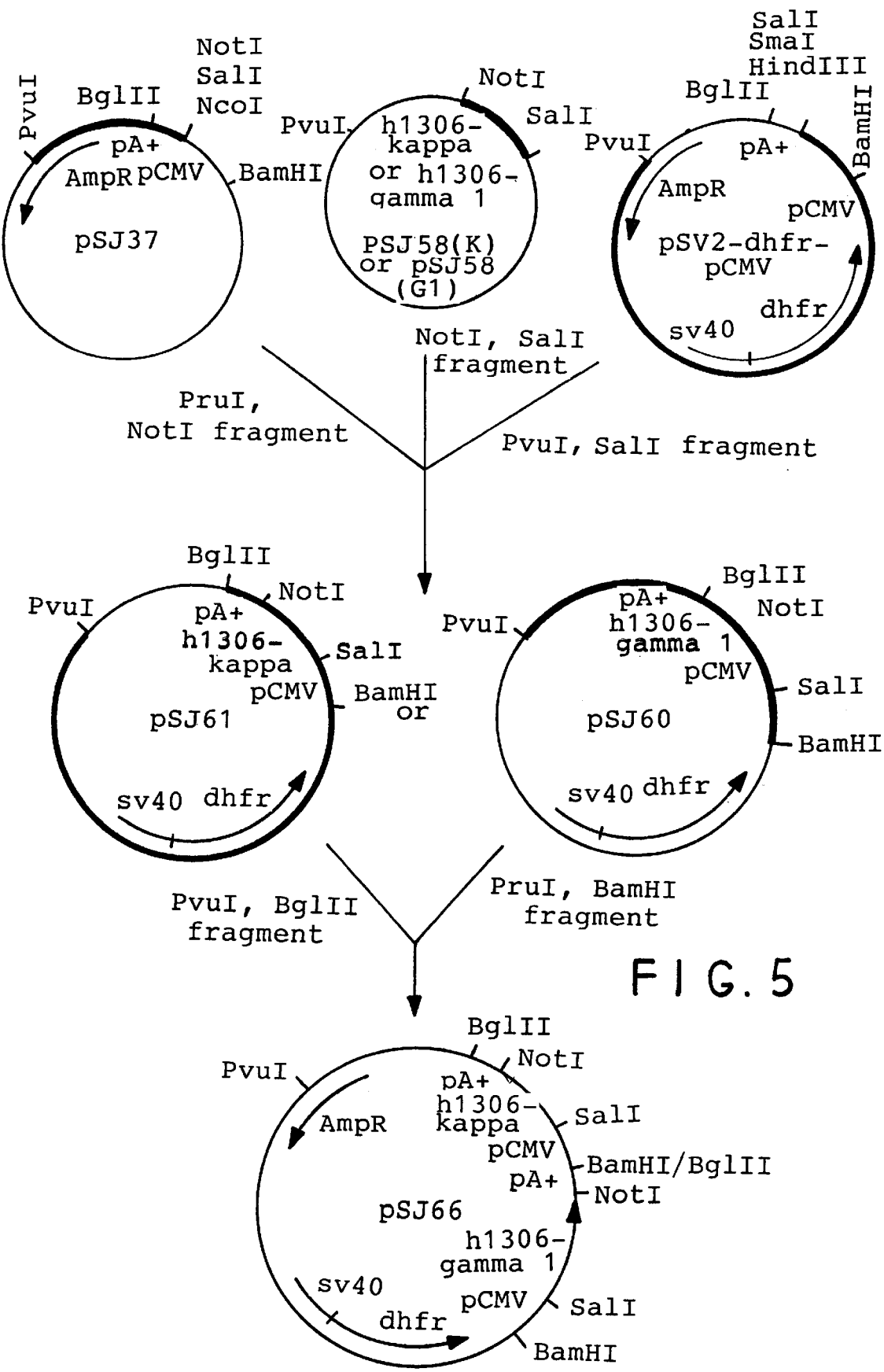
FIG. 5 depicts the plasmid construction of the expression vectors for Humanized 1308.

Finally pSJ60 and pSJ61 were combined into a single plasmid containing both the light and heavy chains and expression signals. This was accomplished by isolating a PvuI-Bam HI fragment from pSJ61 carrying the light chain with a PvuI-Bgl II fragment from pSJ60 carrying the heavy chain to generate pSJ66. (See FIG. 5).

EXAMPLE 4
Transfection of Cosl cells with PSJ60 and PSJ61

Transfections were carried out according to the method of McCutchan and Pagano (J. Nat. Can. Inst. 41: 351–356, 1968) with the following modifications. COS 1 cells (ATCC CRL1650) were maintained in a humidified 5% C02 incubator in 75 cm² tissue culture flasks in Dulbecco's Modified Eagle Medium (DMEM, GIBCO #320-1965) supplemented with 10% Fetal Bovine Serum (FBS, GIBCO #200-6140) and 2 mM L-glutamine (BRL #320-5030) and passed at a split ratio of 1:20 when the cells had reached confluence. 48 hours prior to transfection, 5 100 mm tissue culture dishes were seeded with 1.5×10⁶ cells per dish in 12 ml DMEM, 10% FBS, 2 mM L-glutamine, 1% penicillin-streptomycin (P-S, GIBCO #600-5070). The day of the transfection, 120 ug each of the plasmids pSJ60 and pSJ61 were combined, ethanol precipitated, and aseptically resuspended in 2.5 ml Tris-Buffered-Saline. The resuspended DNA was added dropwise, with mixing, to 10 ml of DMLEM containing 1 mg/ml DEAE-dextran (Phamiacia #17-0350-01) and 250 uM chloroquine (Sigma #C6628). The medium was removed from the COS1 cells in the 100 mm dishes and the cells were washed once with Dulbecco's phosphate buffered saline (D-PBS, GIBCO #310-4190), and 2.5 ml DMEM supplemented with 10% NuSerum (Collaborative Research #55000) were added to each plate. 2.5 ml of the DNA/DEAE-dextran/chloroquine mix were added dropwise to each plate, the plates swirled to mix the DNA, and were returned to the incubator. After 4 hours in the incubator, the supernatant was aspirated from the cells and the cells were washed once with 5 ml D-PBS. The cells were shocked for 3 minutes by the addition of 5 ml of 10% dimethylsulfoxide (DMSO) in D-PBS at room temperature. The DMSO was aspirated from the cells and the cells were washed with 5 ml D-PBS. 14 ml of DMEM/10% FBS/2 mM L-glutamine/1% P-S were added to each plate and the plates were returned to the incubator.

Three days post-transfection the medium was removed from the plates, pooled, and stored at −20° C. The cells were harvested, pooled, and seeded into 4 150 cm² tissue culture flasks two with 40 ml DMEM/10% NuSerum and two with 40 ml DMEM/10% FBS/2 mM L-glutamine. The medium was collected and the cells refed at 7, 10, and 14 days. In this way a total of 125 ug of humanized 1308F antibody was accumulated in 310 ml of medium supplemented with FBS and 85 ug in 240 ml of medium supplemented with NuSerum.

EXAMPLE 5
Transfections of COS 1 cells with PSJ66

48 hours prior to transfection, 5 100 mm tissue culture dishes were seeded with 1.5×10⁶ cells per dish in 12 ml DMEM, 10% FBS, 2 mM L-glutamine, 1% penicillin-streptomycin (P-S, GIBCO #600-5070). The day of the transfection, 125 ug of the plasmid pSJ66 were ethanol precipitated and aseptically resuspended in 1.0 ml Tris-Buffered-Saline. The resuspended DNA was added dropwise, with mixing, to 4.0 ml of DMEM containing 1 mg/ml DEAE-dextran (Pharmacia #17-0350-01) and 250 uM chloroquine (Sigma #C6628). The medium was removed from the COS1 cells in the 100mm dishes and the cells were washed once with Dulbecco's phosphate buffered saline (D-PBS, GIBCO #310-4190), and 2.5 ml DMEM supplemented with 10% NuSerum (Collaborative Research #55000) were added to each plate. 2.5 ml of the DNA/DEAE-dextran/chloroquine mix were added dropwise to each plate, the plates swirled to mix the DNA, and were returned to the incubator. After 4 hours in the incubator, the supernatant was aspirated from the cells and the cells were washed once with 5 ml D-PBS. The cells were shocked for 3 minutes by the addition of 5 ml of 10% dimethylsulfoxide (DMSO) in D-PBS at room temperature. The DMSO was aspirated from the cells and the cells were washed with 5 ml D-PBS. 14 ml of DMEM/10% FBS/2 mM L-glutamine/1% P-S were added to each plate and the plates were returned to the incubator.

Three days post-transfection the medium was removed from the plates, pooled, and stored at −20° C. The cells were harvested, pooled, and seeded into 4 150 cm² tissue culture flasks two with 40 ml DMEM10% NuSerum and two with 40 ml DMEM10% FBS/2 mM L-glutamine. The medium was collected and the cells refed at 7, 10, and 14 days. In this way a total of 190ug of humanized 1308F antibody was accumulated in 310 ml of medium supplemented with FBS and 120 ug in 240 ml of medium supplemented with NuSerum.

The concentration of humanized 1308F antibody secreted from the Cosl cells into the medium was determined using a capture ELISA. Goat anti-human IgG Fc coated onto 96 well plates was used to capture the humanized antibody.

EXAMPLE 7
Generation of a CDR-grafted A-site antibody 1129

Poly-A+ RNA was purified from a lysate of 2×107 murine 1129 hybridoma cells using oligo-dt cellulose. First strand CDNA was made from 1 ug pA+ RNA using random hexamer primers and AMV reverse transcriptase" 1 ug pA+ RNA, 50 mM Tris-HCl pH 8.5, 8 mM $Mg_2Cl$, 30 mM KCl, 1 mM dithiothrietol, 1 mM dNTP's, 25 units of placental ribonuclease inhibitor, 33 uM random hexamer and 10 units of AMV reverse transcriptase for one hour at 42° C. The cDNA from the 1129 VL region was amplified by PCR using oligonucleotides SJ41 and SJ11, see Table 1. cDNA from the 1129 VH region was similarly amplified using oligonucleotides SJ42 and SJ10, see Table 1.

TABLE 1

SJ10
AGCGGATCCAGGGGCCAGTGGATAGAC (SEQ ID NO: 1)
SJ11
GATGGATCCAGTTGGTGCAGCATC (SEQ ID NO: 5)
SJ41
CACGTCGACATTCAGCTGACCCAGTCTCCA (SEQ ID NO: 6)
SJ42
CGGAATTCAGGTIIAICTGCAGIAGTC(A,T)GG (SEQ ID NO: 7)
(I = deoxy-Inosine)
SJ53
CCCAAGCTTGGTCCCCCCTCCGAACGTG (SEQ ID NO: 8)
SJ154
GGCGTCGACTCACCATGGACATGAGGGTCC(C/T)CGCTCAGC (SEQ ID NO: 9)
SJ155 (H1129L CDR 1)
GTCACCATCACTTGCAAGTGCCAGCTGAGTGTAGGTTACATGCACTGGTACC
AGCAG (SEQ ID NO: 10)
SJ157 (H1129L CDR 3)
GCAACTTATTACTGCTTTCAGGGGAGTGGGTACCCATTCACGTTCGGAGGGG
GG (SEQ ID NO: 11)
SJ168
GTGACCAACATGGACCCTGCTGATACTGCCAC (SEQ ID NO: 12)
SJ169
CCATGTTGGTCACTTTAAGGACCACCTGG (SEQ ID NO: 13)
SJ170
CCAGTTTACTAGTGTCATAGATCAGGAGCTTAGGGGC (SEQ ID NO: 14)
SJ171
TGACACTAGTAAACTGGCTTCTGGGGTCCCATCAAGG (SEQ ID NO: 15)

Peroxidase conjugated goat anti-human whole IgG developed with a chromogenic substrate was then used to detect the bound antibody. A purified human IgG1/Kappa preparation was used to calibrate the assay.

EXAMPLE 6
Neutralization of RSV with humanized 1308F

METHODS:

RSV was neutralized with either humanized 1308F from Cos cell supernatant or purified 1308F murine monoclonal antibody. This was done by incubating 50 plaque-forming units of RSV with serial 2-fold dilutions of antibody for 1.0 hour at 37° C. Confluent monolayers of Hep2 cells in 24 well panels were infected with 100 μl of antibody treated virus, untreated control virus, and mock infected controls. Incubated for 1.5 hours at 37° C., humidified , tand 5% $CO_2$ and overlayed with 1.5 mL EMEM, 1% FBS, and 1% methyl cellulose. Cells were fixed and stained with glutaldehyde and crystal violet on day 4. Plaques were counted in triplicate wells and plotted as percent neutralization. The results shown in FIG. 6 indicate that both the purified murine 1308F monoclonal and the humanized 1308F monoclonal antibody at 5 to 10 ng per well yield similar 50% reductions in RSV plaques.

PCR conditions 0.5 uL of 1st strand CDNA, 10 mM Tris-HCl pH8.3, 50 mM KCl, 1.5 mM Mg2Cl, 0.2 mM dNTP's, 0.001% gelatin, 1 uM each primer, 1 ng DNA template and 2.5 u AmpliTaq (TM) DNA polymerase (Perkin Elmer—Cetus). 94° 1 minute, 55° 2 minutes, 72° 2 minutes in Perkin Elmer 480 thermocycler for 25 cycles. The resulting DNA fragment(s) were then extracted once with phenol/chloroform (1/1), precipitated with 2.5 volumes of ETOH, resuspended in the appropriate restriction endonuclease buffer and digested with restriction endonucleases to produce cohesive ends for cloning. The resulting fragments were then separated by electrophoresis on a 1% agarose gel. After staining the gel with ethidium bromide the fragments were excised and purified from the agarose by freezing and extraction in the presence of phenol.

The fragments were then digested with restriction endonucleases EcoRl and BamHl and cloned into plasmid pUC18. The inserts were then sequenced by the dideoxy-nucleotide chain termination method using modified T7 DNA polymerase (Seqeunase, US Biochemical). The translated sequences were compared to human antibody protein sequences. The VL was found to be most homologous to the K102 light chain and the VH was found to be most homologous to the Cor VH region. The 1129 Fv region was then modeled by substitution of the residues from the 1129 VL and VH sequence into the coordinates of corresponding residues in the crystal structure the MCPC603 antibody. Residues were identified as being integral to the folded structure or solvent exposed by visual inspection of the model.

Several residues which were integral and which were different in the mouse and human sequences were left as the mouse residue in order to maintain the integrity of the Fv and thus the binding site. Such residues were 31,83,113, and 116 on the VH and 47 in the VL region. The resulting sequences are shown in FIGS. 7 and 8.

The designed humanized 1129 VH was constructed using synthetic oligonucleotides SJ147–SJ153 (FIG. 9) (SEQ ID NO:36–42) which were combined using PCR. The products of this PCR were then digested with NcoI and SacI and cloned into pladmid vector pSJ40 which is a pUC18 derivative in which an out of frame lacZ1 segment is restored in frame as a fusion to an in-frame V region segment when such a segment is inserted as an NcoI-SacI fragment. A plasmid containing an insert in which 5 mutations were clustered in a single 50 bp region was then subjected to repair of these changes using recombinant PCR and the primers SJ168 and SJ169, see Table 1.

The VL was generated by site directed mutagenesis of the humanized 1308F light chain gene. Oligonucleotides SJ155, see Table 1, (CDR1), and SJ157 (CDR3) were used to separately mutagenize the H1308L gene. Mutagenesis was carried out using T7 DNA polymerase on uracil containing single stranded DNA templates generated in *E. coli* strain BW313 (dut–,ung–) and subsequently transformed into *E. coli* strain DH5 (dut+,ung+). The two mutants were combined and CDR2 introduced by recombinant PCR using oligonucleotides SJ170, SJ154, see Table 1, (5' end) and SJ171, SJ53, see Table 1, (3' end). The CDR-grafted VH and VL genes were placed into pSJ60 (see Example 3) and pSJ61 (see Example 3), respectively as NcoI-SacI fragments in place of the H1308F Vregion segments resulting in plasmids pSJ81 and pSJ105. In addition the murine VH and VL cDNA segments were similarly joined to human C-Gammal and CKappa respectively to generate expression vectors pSJ75 and pSJ84.

EXAMPLE 8
Hu1129 Transient Expression

COS1 cells (ATCC CRL1650) were maintained in a humidified 5% $CO_2$ incubator in 75 $CM^2$ tissue culture flasks in Dulbecco's Modified Eagle Medium (DMEM, GIBCO #320-1965) supplemented with 10% fetal bovine serum (FBS, GIBCO #200-6140) and 2 mM L-glutamine (GIBCO #320-5030) and passed at a split ratio of 1:20 just prior to reaching confluence.

Transfections were carried out according to the method of McCutchan and Pagano (J. Nat. Can. Inst. 41: 351–356, 1968) with the following modifications. Twenty four hours prior to transfection 100 mm tissue culture dishes (Corning #25020) were seeded with 2×106 COS1 cells per dish in 14 ml DMEM, 10% FBS, 2 mM L-glutamine. The day of the transfection 10 ug of the Hu1129 heavy chain plasmid (pSJ81, from Example 7 were combined with 10 ug of the Hu1129 kappa light chain plasmid pSJ105, from Example 7, the DNA was ethanol precipitated and aseptically resuspended in 1.0 ml Tris-Buffered-Saline. The resuspended DNA was added dropwise, with mixing, to 4.0 ml of DMEM containing 1 mg/ml DEAE-dextran (Pharmacia #170350-01) and 250 uM Chloroquine (Sigma #C6628). The medium was removed from the COS1 cell dishes, the cell monolayers were washed once with 10 ml Dulbecco's phosphate buffered saline (D-PBS, GIBCO #310-4190), and 2.5 ml DMEM supplemented with 10% NuSerum (Collaborative Research #55000) and 2 mM L-glutamine were added to each plate. 2.5 ml of the DNA/DEAEdextran/chloroquine mix were added dropwise to each plate, the plates were swirled to mix the DNA, and returned to the incubator. After an eight hour DNA adsorption period the plates were removed from the incubator and the supernatant was aspirated from the plates. The cells were shocked by the addition of 5 ml of 10% DMSO in D-PBS per plate for 3 minutes at room temperature, after which the DMSO was aspirated from the cells and the cells were washed once with 5 ml D-PBS. 15 ml DMEM, 10% NuSerum, 2 mM L-glutamine (production medium) were added to each plate and the plates were returned to the incubator.

Seventy two hours post-transfection the conditioned medium was harvested from the plates and stored at –20° C., and1 5 ml production medium was added to the plates and the plates were returned to the incubator. Ninety six hours later the medium was collected from the plates and stored at 20° C.

EXAMPLE 9
Quantitation of Hu1129

Quantitation of the Hu1129 IgGl antibody secreted into the medium by the COS1 cells was performed using a sandwich type ELISA. In brief, Nunc Maxisorp Immunoplates (Nunc #439454) were coated with 50 ul/well of 0.5 ug/ml goat anti-human IgG Fc (Cappel #55071) in 0.1M sodium bicarbonate pH 9.6 for 3 hours at room temperature. The wells were washed three times with 0.01M sodium phosphate pH 7.4, 0.15M NaCl, 0.1% Tween 20 (PBS-T). Nonspecific protein binding to the plate was blocked by treatment of the wells with 200 ul/well of 3% (w/v) nonfat dry milk in PBS for 30 minutes at room temperature. A purified human IgGl kappa standard (Sigma #1-3889) was made up at 100 ng/ml in PBS-T and serially diluted 1:2 to 1.56 ng/ml, and 50 ul of each were added to duplicate wells of the assay plate. COS1 cell supernatants were diluted in PBS-T and duplicate 50 ul samples were added to the plate. After an one hour room temperature incubation the wells were evacuated and washed three times with PBS-T. To detect the presence of bound Hu1129 antibody, horseradish peroxidase conjugated affinity purified goat anti-human IgG (whole molecule, Cappel #3601-0081) was diluted 1:1000 in PBS-T and 50 ul was added to each well of the assay plate and incubated at room temperature for one hour. The plate was washed three times with PBS-T and 100 ul of the chromogenic substrate TMBlue (TSI #TM102) was added to each well. The plate was incubated at room temperature in the dark for ten minutes and the reaction was stopped by the addition of 50 ul per well of 4.5M $H_2SO_4$. The plate was read at 450 nm using a Molecular Devices Vmax microplate reader, and data analysis was performed using Softmax software (Molecular Devices) running on an IBM P/S2 model 80 computer.

During the first seventy two hours of production the COS1 cells produced 0.06 ug/ml Hu1129, for a total of 0.9 ug. In the next ninety six hours of production the COS1 cells produced 0.99 ug/ml Hu1129, for a total of 14.85 ug.

EXAMPLE 10
Hu1129 Binding Assay

Binding assays of the Hu1129 were performed in a capture ELISA, essentially as for the quantitation ELISA, but with the following changes. Plates were coated with the Mul 331 antibody at 0.5 ug/well, the wells were blocked with 3% non-fat milk in PBS-T, and 50 ul of RSV infected HEP2 cell lysate was added to each well and incubated at room temperature for 1 hour. The remainder of the assay was carried out as for the quantitation assay starting with the addition of diluted samples to the wells. Results were analyzed as a double reciprocal plot of OD vs antibody concentration from which an apparent Kd for the H1129 molecule of 0.7 nM was determined compared to 10 nM for the M1129HuGamma1,Kappa antibody.

RSV neutralization assays on H1129 and ch1129 antibody were performed according to the following procedure:
1. Unwrap 96 well Costar cell culture plates in hood.
2. Warm Growth Medium (GM) to 37° C.
3. Thaw MA104 cells at 37° C. Dilute to ~150,000 cells per mL with GM. Mix cells and dispense 200 µl per well.
4. Culture cells 37° C., 5% $CO_2$, and humidified overnight before infection.
5. Dilute RSV Stock to 10,000 pfu per mL in Maintenance Medium (MM).
6. Mix equal volume of Antibody diluted in MM with equal volume of diluted RSV. Incubate at 37° C., 5% $CO_2$, and humidified for 1.0 h before infection.
7. Infect replicate wells of MA104 cells with 200 µl of the Antibody and Virus mixture. Infect replicate wells with virus and mock infected controls.
8. Wrap the plates in cellophane and incubate at 37° C., 95% humidity, and 5% $CO_2$ for 5 days.
9. ELISA for RSV: Aspirate each well; add 100 µl 80% Acetone/PBS (vol./vol.) and incubate at room temperature 30 minutes.
10. Aspirate each well and air dry for 30 minutes on the grill of a laminar flow hood.
11. Wash 4 times with PBS, 0.05% Tween 20.
12. Add 100 µl of monoclonal antibody to RSV F-protein to each well. Incubate for 1.0 h at 37° C.
13. Wash 4 times with PBS, 0.05% Tween 20.
14. Add 100 µl of anti-murine antibody goat serum-horse radish peroxidaze conjugate to each well. Incubate for 1.0 h at 37° C.
15. Wash 4 times with PBS, 0.05% Tween 20.
16. Add 100 µl of a freshly prepared 1:1 mixture of ABTS and peroxide to each well. Incubate at room temperature until the optical density (405 nm) of the virus control is 5 to 10 times that of the mock infected controls.

Appendix:
Growth Medium (GM): Minimum Essential Medium (Eagle) with
Earle's BSS,
2 mM glutamine,
Eagle's non-essential amino acids 0.1 mM final,
Fetal bovine serum 10% (v/v),
Penicillin 50 units/ml,
Streptomycin 50 mcg/ml
Maintenance Medium (MM): as above with serum reduced to 1 to 2%.
MA104 cell stocks are grown up in T150 flasks with Growth Medium. Stocks are frozen at $3 \times 10^6$ cells per 1.8 mL vial in 10% DMSO and Growth Medium. Stored in a $LN_2$ refrigerator.
RSV stocks: are grown up in MA104 (monkey kidney) or Hep 2 cells in T150 flasks. Add ~0.2 ml (~100,000 pfu) virus stock per confluent T150. Adsorption for 1.0 h at room temperature. Then add 20 mL maintenance medium with 1% fetal bovine serum. Incubate 4–5 days at 37° C. Collect cells just before 100% cpe by scraping. Spin down cells; remove all but 10 mL of supernatant. Freeze (dry ice-ethanol bath) thaw cell pellet, vortex, re-freeze, and store virus stock in LN2 refrigerator.

ELISA Antibody Buffer: PBS, 0.05% Tween 20 (w/v), 2.0% goat serum (v/v) and 0.5% gelatin (w/v).
RSV F Protein Antibody: Chemicon Mab 858-1 anti-RSV fusion protein diluted ~1:5000 in ELISA Antibody Buffer.
Anti-Murine Serum.: Fisher horse radish peroxidase conjugated to goat anti-mouse IgG (Heavy Chain Specific) diluted ~1:4000 in ELISA Antibody Buffer.

The results are shown in FIG. 10, and indicate 25 ng/ml achieved 50% neutralization in this assay while 45 ug/ml of the ch1129 antibody was required for 50% neutralization in this experiment. Over a series of 6 separate assays the mean 50% neutralization value for H1129 was 17 ng/ml. As a control and to compare potency we also assayed a polyclonal human IgG preparation made from the plasma of individuals with high neutralizing titers for RSV. This preparation, termed RSVig (lot#4), gave a mean 50% neutralization value of 2.3 ug/ml over 3 experiments. Thus the H1129 is 100-fold more potent in this assay as the enriched polyclonal preparation.

EXAMPLE 11

Kinetic Analysis of Humanized RSV Mabs by BlAcoreTM

The kinetics of interaction between humanized RSV Mabs and the RSV F protein was studied by surface plasmon resonance using a Pharmacia BlAcoreTM biosensor. A recombinant baculovirus expressing a C-terminal truncated F protein provided an abundant source of antigen for kinetic studies. The supernatant, which contained the secreted F protein, was enriched approximately 20-fold by successive chromatography on concanalvalin A and Q-sepharose columns. The pooled fractions were dialyzed against 10 mM sodium citrate (pH 5.5), and concentrated to approximately 0.1 mg/ml. An aliquot of the F-protein (100 ml) was amine-coupled to the BlAcore sensor chip. The amount immobilized gave approximately 2000 response units (Rmax) Of signal when saturated with either H1129 or H1308F. This indicated that there was an equal number of "A" and "C" antigenic sites on the F-protein preparation following the coupling procedure. Two unrelated irrelevant Mabs (RVFV 4D4 and CMV H758) showed no interation with the immobolized F protein. A typical kinetic study involved the injection of 35 ml of Mab at varying concentrations (25–300 nM) in PBS buffer containing 0.05% Tween-20 (PBS/Tween). The flow rate was maintained at 5 ml/min, giving a 7 min binding phase. Following the injection of Mab, the flow was exchanged with PBS/Tween buffer for 30 min for determining the rate of dissociation. The sensor chip was regenerated between cycles with a 2 min pulse of 10 mM HCl. The regeneration step caused a minimal loss of binding capacity of the immobilized F-protein (4% loss per cycle). This small decrease did not change the calculated values of the rate constants for binding and dissociation.

The affinity of the various Mabs for binding to the F protein was calculated from the ratio of the first order rate constant for dissociation to the second order rate constant for binding ($K_d = k_{diss}/k_{assoc}$). The value for $k_{assoc}$ was calculated based on the following rate equation:

$$dR/dt = k_{assoc}[Mab]R_{max} - (k_{assoc}[Mab] + k_{diss})R \qquad (1)$$

where R and Rmax are the response units at time t and infinity, respectively. A plot of dr/dt as a function of R gives a slope of ($k_{assoc}[Mab] + k_{diss}$)—Since these slopes are linearly related to the [Mab], the value $k_{assoc}$ can be derived from a replot of the slopes versus [Mab]. The slope of the new line is equal to kassoc. Although the value of kdiss can be extrapolated from the Y-intercept, a more accurate value was determined by direct measurement of $k_{diss}$. Following the injection phase of the Mab, PBS/Tween buffer flows across the sensor chip. From this point, [Mab]=0. Equation (1) thus reduces to:

$$dr/dt = k_{diss}r \text{ or } dR/R = k_{diss}dt \qquad (2)$$

Integration of equation (2) gives:

$$ln(R_0/R_t) = k_{diss}t \qquad (3)$$

where $R_0/R_t$ are the response units at time 0 (start of dissociation phase) and t, respectively. Lastly, plotting $ln(R_0/R_t)$ as a function of t gives a slope of kdiss.

| | Kinetic Constants for RSV Mabs | | | |
|---|---|---|---|---|
| Mab | ka(assoc) $M^{-1}sec^{-1}$ | kd(dissoc) $sec^{-1}$ | $t_{1/2}$# (Hrs) | $K_d(k_d/k_a)$ nM |
| CH1129 | $5.0 \times 10^{-5}$ | $7.5 \times 10^{-5}$ | 2.6 | 1.5 |
| H1129 | $4.9 \times 10^{-4}$ | $6.9 \times 10^{-5}$ | 2.8 | 1.4 |
| M1129 | $3.5 \times 10^{-4}$ | $4.0 \times 10^{-4}$ | 0.48 | 11.4 |
| M1308F | $3.5 \times 10^{-4}$ | $3.8 \times 10^{-5}$ | 5.1 | 1.1 |
| H1308F | $2.2 \times 10^{-4}$ | $5.5 \times 10^{-5}$ | 3.5 | 2.5 |

References

1. Hall, C. B., Doiuglas, R. G., Geiman, J. M. et al., N.Engl.J.Med. 293:1343, 1975.

2. Hall, C. B., McBride, J. T., Walsh, E. E. et al., N.Engl.J.Med. 308:1443, 1983.

3. Hall, C. B., McBride, J. T., Gala, C. L. et al., JAMA 254:3047, 1985.

4. Wald, E. R., et al., J.Pediat. 112:154, 1988.

5. Kapikian, A. Z., Mithcell, R. H., Chanock, R. M. et al., Am.J.Epidemiol. 89:405, 1969.

6. Prince, G. A., Hemming, V. G., Horswood, R. L. et al., Virus Res. 3:193, 1985.

7. Hemming, V. G., Prince, G. A., Horswood, R. L. et al., J.Infect.Dis. 152:1083, 1985.

8. Wright, P. F., Belshe, R. B., et al., Infect.Immun. 37:397, 1982.

9. Conrad, D. A., Christenson, J. C., et al., Peditr.Infect-.Dis.J. 6:152, 1987.

10. LoBuglio, A. F., Wheeler, R. L., Trang, J. et al., Proc.Natl.Acad. Sci. 86:4220, 1989.

11. Steplewski, Z., Sun, L. K., Shearman, C. W. et al., Proc.Natl.Acad. Sci. 85:4852, 1988.

12. Boulianne, G. L., Hozumi, N., Shulman, M. J. Nature. 312:643, 1984.

13. Sun, L. K., Curtis, P., Rakowicz-Szulczynska, E. et al., Proc.Natl.Acad. Sci. 84:214, 1987.

14. Liu, A. Y., Mack, P. W., Champion, C. I., Robinson, R. R., Gene 54:33, 1987.

15. Morrison, S. L., Johnson, M. J., Hersenber, L. A., Oi, V. T. Proc.Natl.Acad. Sci. 81:6851, 1984.

16. Morrison, S. L. Science 229:1202, 1985.

17. Sahagan, B. G., Dorai, H., Saltzgaber-Muller, J. et al., J.Immunol. 137:1066, 1986.

18. Taked, S., Naito, T., Hama, K., Noma, T., Honjo, T., Nature 314:452, 1985.

19. Carson, D. A., Freimark, B. D., Adv. Immunol. 38:275, 1986.

20. Beeler, J. A., et al., J.Virol. 63:2941–2950, 1989.

21. Coelingh, et al., Virology, 143:569–582, 1985.

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
  ( A ) LENGTH: 27 BASE PAIRS
  ( B ) TYPE: NUCLEIC ACID
  ( C ) STRANDEDNESS: SINGLE
  ( D ) TOPOLOGY: LINEAR ( i i ) MOLECULE TYPE: Oligonucleotide ( x i ) SEQUENCE DESCRIPTION: SEQ ID NO:1:

A G C G G A T C C A  G G G G C C A G T G  G A T A G A C    2 7

( 2 ) INFORMATION FOR SEQ ID NO:2:

( i ) SEQUENCE CHARACTERISTICS:
  ( A ) LENGTH: 17 NUCLEOTIDES
  ( B ) TYPE: NUCLEIC ACID
  ( C ) STRANDEDNESS: SINGLE
  ( D ) TOPOLOGY: LINEAR ( i i ) MOLECULE TYPE: Oligonucleotide ( x i ) SEQUENCE DESCRIPTION: SEQ ID NO:2:

TGGATGGTGG GAAGATG                                                                                    17

( 2 ) INFORMATION FOR SEQ ID NO:3:

( i ) SEQUENCE CHARACTERISTICS:
           ( A ) LENGTH: 15 NUCLEOTIDES
           ( B ) TYPE: NUCLEIC ACID
           ( C ) STRANDEDNESS: SINGLE
           ( D ) TOPOLOGY: LINEAR ( i i ) MOLECULE TYPE: Oligonucleotide ( x i ) SEQUENCE DESCRIPTION: SEQ ID NO:3:

GGCCAGTGGA TAGAC                                                                                      15

( 2 ) INFORMATION FOR SEQ ID NO:4:

( i ) SEQUENCE CHARACTERISTICS:
           ( A ) LENGTH: 16 NUCLEOTIDES
           ( B ) TYPE: NUCLEIC ACID
           ( C ) STRANDEDNESS: SINGLE
           ( D ) TOPOLOGY: LINEAR ( i i ) MOLECULE TYPE: Oligonucleotide ( x i ) SEQUENCE DESCRIPTION: SEQ ID NO:4:

TACAGTTGGT GCAGCA                                                                                     16

( 2 ) INFORMATION FOR SEQ ID NO:5:

( i ) SEQUENCE CHARACTERISTICS:
           ( A ) LENGTH: 24 NUCLEOTIDES
           ( B ) TYPE: NUCLEIC ACID
           ( C ) STRANDEDNESS: SINGLE
           ( D ) TOPOLOGY: LINEAR ( i i ) MOLECULE TYPE: Oligonucleotide ( x i ) SEQUENCE DESCRIPTION: SEQ ID NO:5:

GATGGATCCA GTTGGTGCAG CATC                                                                            24

( 2 ) INFORMATION FOR SEQ ID NO:6:

( i ) SEQUENCE CHARACTERISTICS:
           ( A ) LENGTH: 30 NUCLEOTIDES
           ( B ) TYPE: NUCLEIC ACID
           ( C ) STRANDEDNESS: SINGLE
           ( D ) TOPOLOGY: LINEAR ( i i ) MOLECULE TYPE: Oligonucleotide ( x i ) SEQUENCE DESCRIPTION: SEQ ID NO:6:

CACGTCGACA TTCAGCTGAC CCAGTCTCCA                                                                      30

( 2 ) INFORMATION FOR SEQ ID NO:7:

( i ) SEQUENCE CHARACTERISTICS:
           ( A ) LENGTH: 30 NUCLEOTIDES
           ( B ) TYPE: NUCLEIC ACID
           ( C ) STRANDEDNESS: SINGLE
           ( D ) TOPOLOGY: LINEAR ( i i ) MOLECULE TYPE: Oligonucleotide ( x i ) SEQUENCE DESCRIPTION: SEQ ID NO:7:

CGGAATTCAG GTNNANCTGC AGNAGTCWGG                                                                      30

( 2 ) INFORMATION FOR SEQ ID NO:8:

( i ) SEQUENCE CHARACTERISTICS:
        ( A ) LENGTH: 28 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:8:

CCCAAGCTTG GTCCCCCCTC CGAACGTG     28

( 2 ) INFORMATION FOR SEQ ID NO:9:

( i ) SEQUENCE CHARACTERISTICS:
        ( A ) LENGTH: 39 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:9:

GGCGTCGACT CACCATGGAC ATGAGGGTCC YCGCTCAGC     39

( 2 ) INFORMATION FOR SEQ ID NO:10:

( i ) SEQUENCE CHARACTERISTICS:
        ( A ) LENGTH: 57 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:10:

GTCACCATCA CTTGCAAGTG CCAGCTGAGT GTAGGTTACA TGCACTGGTA CCAGCAG     57

( 2 ) INFORMATION FOR SEQ ID NO:11:

( i ) SEQUENCE CHARACTERISTICS:
        ( A ) LENGTH: 54 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:11:

GCAACTTATT ACTGCTTTCA GGGGAGTGGG TACCCATTCA CGTTCGGAGG GGGG     54

( 2 ) INFORMATION FOR SEQ ID NO:12:

( i ) SEQUENCE CHARACTERISTICS:
        ( A ) LENGTH: 32 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:12:

GTGACCAACA TGGACCCTGC TGATACTGCC AC     32

( 2 ) INFORMATION FOR SEQ ID NO:13:

( i ) SEQUENCE CHARACTERISTICS:
        ( A ) LENGTH: 29 NUCLEOTIDES
        ( B ) TYPE: NUCLEIC ACID
        ( C ) STRANDEDNESS: SINGLE
        ( D ) TOPOLOGY: LINEAR (i i) MOLECULE TYPE: Oligonucleotide (x i) SEQUENCE DESCRIPTION: SEQ ID NO:13:

CCATGTTGGT CACTTTAAGG ACCACCTGG 29

(2) INFORMATION FOR SEQ ID NO:14:

(i) SEQUENCE CHARACTERISTICS:
(A) LENGTH: 37 NUCLEOTIDES
(B) TYPE: NUCLEIC ACID
(C) STRANDEDNESS: SINGLE
(D) TOPOLOGY: LINEAR (i i) MOLECULE TYPE: Oligonucleotide (x i) SEQUENCE DESCRIPTION: SEQ ID NO:14:

CCAGTTTACT AGTGTCATAG ATCAGGAGCT TAGGGGC 37

(2) INFORMATION FOR SEQ ID NO:15:

(i) SEQUENCE CHARACTERISTICS:
(A) LENGTH: 37 NUCLEOTIDES
(B) TYPE: NUCLEIC ACID
(C) STRANDEDNESS: SINGLE
(D) TOPOLOGY: LINEAR (i i) MOLECULE TYPE: Oligonucleotide (x i) SEQUENCE DESCRIPTION: SEQ ID NO:15:

TGACACTAGT AAACTGGCTT CTGGGGTCCC ATCAAGG 37

(2) INFORMATION FOR SEQ ID NO:16:

(i) SEQUENCE CHARACTERISTICS:
(A) LENGTH: 97 AMINO ACIDS
(B) TYPE: AMINO ACID
(D) TOPOLOGY: LINEAR (i i) MOLECULE TYPE: PROTEIN (x i) SEQUENCE DESCRIPTION: SEQ ID NO:16:

Gln Val Gln Leu Val Gln Ser Gly Ala Glu Val Lys Lys Pro Gly
                 5                  10                  15

Ala Ser Val Lys Val Ser Cys Lys Ala Ser Gly Tyr Thr Phe Asn
                20                  25                  30

Ser Tyr Tyr Met His Trp Val Arg Gln Ala Pro Gly Gln Gly Leu
                35                  40                  45

Glu Trp Met Gly Ile Ile Asn Pro Ser Gly Gly Ser Thr Ser Tyr
                50                  55                  60

Ala Gln Lys Phe Gln Gly Arg Val Thr Met Thr Arg Asp Thr Ser
                65                  70                  75

Thr Ser Thr Val Tyr Met Glu Leu Ser Ser Leu Arg Ser Glu Asp
                80                  85                  90

Thr Ala Val Tyr Tyr Cys Ala
                95

(2) INFORMATION FOR SEQ ID NO:17:

(i) SEQUENCE CHARACTERISTICS:
(A) LENGTH: 117 AMINO ACIDS
(B) TYPE: AMINO ACID
(D) TOPOLOGY: LINEAR (i i) MOLECULE TYPE: PROTEIN ( x i ) SEQUENCE DESCRIPTION: SEQ ID NO:17:

| Gln | Val | Gln | Leu | Val | Gln | Ser | Gly | Ala | Glu | Val | Lys | Lys | Pro | Gly |
|-----|-----|-----|-----|-----|-----|-----|-----|-----|-----|-----|-----|-----|-----|-----|
|     |     |     |     | 5   |     |     |     |     | 10  |     |     |     |     | 15  |
| Ala | Ser | Val | Lys | Val | Ser | Cys | Lys | Ala | Ser | Gly | Phe | Asn | Ile | Lys |
|     |     |     |     | 20  |     |     |     |     | 25  |     |     |     |     | 30  |
| Asp | Tyr | Tyr | Ile | Tyr | Trp | Val | Arg | Gln | Ala | Pro | Gly | Gln | Gly | Leu |
|     |     |     |     | 35  |     |     |     |     | 40  |     |     |     |     | 45  |
| Glu | Trp | Ile | Gly | Trp | Ile | Asp | Pro | Glu | Asn | Gly | Asn | Thr | Val | Phe |
|     |     |     |     | 50  |     |     |     |     | 55  |     |     |     |     | 60  |
| Asp | Pro | Lys | Phe | Gln | Gly | Arg | Val | Thr | Met | Thr | Arg | Asp | Thr | Ser |
|     |     |     |     | 65  |     |     |     |     | 70  |     |     |     |     | 75  |
| Thr | Ser | Thr | Val | Tyr | Met | Glu | Leu | Ser | Ser | Leu | Arg | Ser | Glu | Asp |
|     |     |     |     | 80  |     |     |     |     | 85  |     |     |     |     | 90  |
| Thr | Ala | Val | Tyr | Tyr | Cys | Ala | Tyr | Tyr | Gly | Thr | Ser | Ser | Phe | Asp |
|     |     |     |     | 95  |     |     |     |     | 100 |     |     |     |     | 105 |
| Phe | Trp | Gly | Gln | Gly | Thr | Thr | Leu | Thr | Val | Ser | Ser |     |     |     |
|     |     |     |     | 110 |     |     |     |     | 115 |     |     |     |     |     |

( 2 ) INFORMATION FOR SEQ ID NO:18:

( i ) SEQUENCE CHARACTERISTICS:
        ( A ) LENGTH: 117 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:18:

| Glu | Val | Gln | Leu | Gln | Gln | Ser | Gly | Ala | Glu | Leu | Val | Arg | Pro | Gly |
|-----|-----|-----|-----|-----|-----|-----|-----|-----|-----|-----|-----|-----|-----|-----|
|     |     |     |     | 5   |     |     |     |     | 10  |     |     |     |     | 15  |
| Ala | Leu | Val | Lys | Leu | Ser | Cys | Lys | Ala | Ser | Gly | Phe | Asn | Ile | Lys |
|     |     |     |     | 20  |     |     |     |     | 25  |     |     |     |     | 30  |
| Asp | Tyr | Tyr | Ile | Tyr | Trp | Val | Lys | Gln | Arg | Pro | Glu | Gln | Gly | Leu |
|     |     |     |     | 35  |     |     |     |     | 40  |     |     |     |     | 45  |
| Glu | Trp | Ile | Gly | Trp | Ile | Asp | Pro | Glu | Asn | Gly | Asn | Thr | Val | Phe |
|     |     |     |     | 50  |     |     |     |     | 55  |     |     |     |     | 60  |
| Asp | Pro | Lys | Phe | Gln | Gly | Lys | Ala | Ser | Ile | Thr | Ser | Asp | Thr | Ser |
|     |     |     |     | 65  |     |     |     |     | 70  |     |     |     |     | 75  |
| Ser | Asn | Thr | Ala | Tyr | Leu | Gln | Leu | Ser | Ser | Leu | Thr | Ser | Glu | Asp |
|     |     |     |     | 80  |     |     |     |     | 85  |     |     |     |     | 90  |
| Thr | Ala | Val | Tyr | Tyr | Cys | Ala | Tyr | Tyr | Gly | Thr | Ser | Ser | Phe | Asp |
|     |     |     |     | 95  |     |     |     |     | 100 |     |     |     |     | 105 |
| Phe | Trp | Gly | Gln | Gly | Thr | Thr | Leu | Thr | Val | Ser | Ser |     |     |     |
|     |     |     |     | 110 |     |     |     |     | 115 |     |     |     |     |     |

( 2 ) INFORMATION FOR SEQ ID NO:19:

( i ) SEQUENCE CHARACTERISTICS:
        ( A ) LENGTH: 95 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:19:

| Asp | Ile | Gln | Met | Thr | Gln | Ser | Pro | Ser | Thr | Leu | Ser | Ala | Ser | Val |
|-----|-----|-----|-----|-----|-----|-----|-----|-----|-----|-----|-----|-----|-----|-----|
|     |     |     |     | 5   |     |     |     |     | 10  |     |     |     |     | 15  |
| Gly | Asp | Arg | Val | Thr | Ile | Thr | Cys | Arg | Ala | Ser | Gln | Ser | Ile | Ser |
|     |     |     |     | 20  |     |     |     |     | 25  |     |     |     |     | 30  |

| Ser | Trp | Leu | Ala | Trp<br>35 | Tyr | Gln | Gln | Lys | Pro<br>40 | Gly | Lys | Ala | Pro | Lys<br>45 |
|-----|-----|-----|-----|-----|-----|-----|-----|-----|-----|-----|-----|-----|-----|-----|
| Leu | Leu | Ile | Tyr | Asp<br>50 | Ala | Ser | Ser | Leu | Glu<br>55 | Ser | Gly | Val | Pro | Ser<br>60 |
| Arg | Phe | Ser | Gly | Ser<br>65 | Gly | Ser | Gly | Thr | Glu<br>70 | Phe | Thr | Leu | Thr | Ile<br>75 |
| Ser | Ser | Leu | Gln | Pro<br>80 | Asp | Asp | Phe | Ala | Thr<br>85 | Tyr | Tyr | Cys | Gln | Gln<br>90 |
| Tyr | Asn | Ser | Tyr | Ser<br>95 | | | | | | | | | | |

( 2 ) INFORMATION FOR SEQ ID NO:20:

( i ) SEQUENCE CHARACTERISTICS:
        ( A ) LENGTH: 107 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:20:

| Asp | Ile | Gln | Met | Thr<br>5 | Gln | Ser | Pro | Ser | Thr<br>10 | Leu | Ser | Ala | Ser | Val<br>15 |
|-----|-----|-----|-----|-----|-----|-----|-----|-----|-----|-----|-----|-----|-----|-----|
| Gly | Asp | Arg | Val | Thr<br>20 | Ile | Thr | Cys | Lys | Ala<br>25 | Ser | Gln | Asp | Ile | Asn<br>30 |
| Arg | Tyr | Leu | Asn | Trp<br>35 | Tyr | Gln | Gln | Lys | Pro<br>40 | Gly | Lys | Ala | Pro | Lys<br>45 |
| Leu | Leu | Ile | Tyr | Arg<br>50 | Ala | Asn | Arg | Leu | Val<br>55 | Asp | Gly | Val | Pro | Ser<br>60 |
| Arg | Phe | Ser | Gly | Ser<br>65 | Gly | Ser | Gly | Thr | Glu<br>70 | Phe | Thr | Leu | Thr | Ile<br>75 |
| Ser | Ser | Leu | Gln | Pro<br>80 | Asp | Asp | Phe | Ala | Thr<br>85 | Tyr | Tyr | Cys | Leu | Gln<br>90 |
| Phe | His | Glu | Phe | Pro<br>95 | Tyr | Thr | Phe | Gly | Gly<br>100 | Gly | Thr | Lys | Leu | Glu<br>105 |
| Ile | Lys | | | | | | | | | | | | | |

( 2 ) INFORMATION FOR SEQ ID NO:21:

( i ) SEQUENCE CHARACTERISTICS:
        ( A ) LENGTH: 107 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:21:

| Asp | Ile | Lys | Met | Thr<br>5 | Gln | Ser | Pro | Ser | Ser<br>10 | Met | Tyr | Val | Ser | Leu<br>15 |
|-----|-----|-----|-----|-----|-----|-----|-----|-----|-----|-----|-----|-----|-----|-----|
| Gly | Glu | Arg | Val | Thr<br>20 | Ile | Thr | Cys | Lys | Ala<br>25 | Ser | Gln | Asp | Ile | Asn<br>30 |
| Arg | Tyr | Leu | Asn | Trp<br>35 | Phe | Gln | Gln | Lys | Pro<br>40 | Gly | Lys | Ser | Pro | Lys<br>45 |
| Thr | Leu | Ile | His | Arg<br>50 | Ala | Asn | Arg | Leu | Val<br>55 | Asp | Gly | Val | Pro | Ser<br>60 |
| Arg | Phe | Ser | Gly | Ser<br>65 | Gly | Ser | Gly | Gln | Glu<br>70 | Tyr | Ser | Leu | Thr | Ile<br>75 |
| Ser | Ser | Leu | Glu | Phe<br>80 | Glu | Asp | Met | Gly | Ile<br>85 | Tyr | Tyr | Cys | Leu | Gln<br>90 |

| Phe | His | Glu | Phe | Pro | Tyr | Thr | Phe | Gly | Gly | Gly | Thr | Lys | Leu | Glu |
|-----|-----|-----|-----|-----|-----|-----|-----|-----|-----|-----|-----|-----|-----|-----|
|     |     |     |     | 95  |     |     |     |     | 100 |     |     |     |     | 105 |

Ile Lys ( 2 ) INFORMATION FOR SEQ ID NO:22:

( i ) SEQUENCE CHARACTERISTICS:
    ( A ) LENGTH: 117 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:22:

```
CCATGGACTG  GACCTGGAGG  GTCTTCTGCT  TGCTGGCTGT  AGCACCAGGT  GCCCACTCCC      60

AGGTGCAGCT  GGTGCAGTCT  GGAGCTGAGG  TGAAGAAGCC  TGGAGCCTCA  GTGAAGG        117
```

( 2 ) INFORMATION FOR SEQ ID NO:23:

( i ) SEQUENCE CHARACTERISTICS:
    ( A ) LENGTH: 120 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:23:

```
CACTTCTTCG  GACCTCGGAG  TCACTTCCAA  AGGACGTTCC  GTAGACCTAA  GTTGTAATTC      60

CTGATGATGT  AAATGACCCA  CGCTGTCCGA  GGACCTGTTC  CCGAGCTCAC  CTACCCAACC     120
```

( 2 ) INFORMATION FOR SEQ ID NO:24:

( i ) SEQUENCE CHARACTERISTICS:
    ( A ) LENGTH: 119 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:24:

```
GGGCTCGAGT  GGATGGGTTG  GATTGACCCT  GAGAATGGTA  ATACTGTGTT  TGACCGAAGT      60

TCCAGGGCAG  AGTCACCATG  ACCAGGACA   CGTCCACGAG  CACAGTCTAC  ATGGAGCTG     119
```

( 2 ) INFORMATION FOR SEQ ID NO:25:

( i ) SEQUENCE CHARACTERISTICS:
    ( A ) LENGTH: 137 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:25:

```
GGTGCTCGTG  TCAGATGTAC  CTCGACTCGT  CGGACTCTAG  ACTCCTGTGC  CGGCACATAA      60

TGACACGCAT  GATGCCATGT  TCGAGGAAAC  TGAAGACCCC  GGTTCCGTGG  TGAGAGTGTC     120

ACTCGAGTAT  TCCTAGG                                                        137
```

( 2 ) INFORMATION FOR SEQ ID NO:26:

( i ) SEQUENCE CHARACTERISTICS:
    ( A ) LENGTH: 106 NUCLEOTIDES ( B ) TYPE: NUCLEIC ACID
( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:26:

```
CCATGGACAT GAGGGTCCCC GCTCAGCTCC TGGGGCTCCT GCTGCTCTGG CTCCCAGGTG      60
CCAAATGTGA TATCCAGATG ACCCAGTCTC CTTCCACCCT GTCTGC                    106
```

( 2 ) INFORMATION FOR SEQ ID NO:27:

( i ) SEQUENCE CHARACTERISTICS:
  ( A ) LENGTH: 107 NUCLEOTIDES
  ( B ) TYPE: NUCLEIC ACID
  ( C ) STRANDEDNESS: SINGLE
  ( D ) TOPOLOGY: LINEAR ( i i ) MOLECULE TYPE: Oligonucleotide ( x i ) SEQUENCE DESCRIPTION: SEQ ID NO:27:

```
GTCAGAGGAA GGTGGGACAG ACGTAGACAT CCTCTGTCTC AGTGGTAGTG AACGTTCCGC      60
TCAGTCCTGT AATTATCCAT AAATTTGACC ATGGTCGTCT TTGGGCC                   107
```

( 2 ) INFORMATION FOR SEQ ID NO:28:

( i ) SEQUENCE CHARACTERISTICS:
  ( A ) LENGTH: 107 NUCLEOTIDES
  ( B ) TYPE: NUCLEIC ACID
  ( C ) STRANDEDNESS: SINGLE
  ( D ) TOPOLOGY: LINEAR ( i i ) MOLECULE TYPE: Oligonucleotide ( x i ) SEQUENCE DESCRIPTION: SEQ ID NO:28:

```
GAAAGCCCCT AAGCTCCTGA TCTATCGTGC AAACAGATTG GTAGATGGGG TCCCATCAAG      60
GTTCAGCGGC AGTGGATCTG GGACAGAATT CACTCTCACC ATCAGCA                   107
```

( 2 ) INFORMATION FOR SEQ ID NO:29:

( i ) SEQUENCE CHARACTERISTICS:
  ( A ) LENGTH: 116 NUCLEOTIDES
  ( B ) TYPE: NUCLEIC ACID
  ( C ) STRANDEDNESS: SINGLE
  ( D ) TOPOLOGY: LINEAR ( i i ) MOLECULE TYPE: Oligonucleotide ( x i ) SEQUENCE DESCRIPTION: SEQ ID NO:29:

```
GTCTTAAGTG AGAGTGGTAG TCGTCGGACG TCGGACTACT AAAACGTTGA ATAATGACGG      60
ATGTCAAAGT ACTCAAAGGC ATGTGCAAGC CTCCCCCCTG GTTCGAACTT TATTTT        116
```

( 2 ) INFORMATION FOR SEQ ID NO:30:

( i ) SEQUENCE CHARACTERISTICS:
  ( A ) LENGTH: 123 AMINO ACIDS
  ( B ) TYPE: AMINO ACID
  ( D ) TOPOLOGY: LINEAR ( i i ) MOLECULE TYPE: PROTEIN ( x i ) SEQUENCE DESCRIPTION: SEQ ID NO:30:

```
Gln Val Thr Leu Arg Glu Ser Gly Pro Ala Leu Val Lys Pro Thr
              5                  10                  15
Gln Thr Leu Thr Leu Thr Cys Thr Phe Ser Gly Phe Ser Leu Ser
             20                  25                  30
```

|     |     |     |     |     |     |     |     |     |     |     |     |     |     |     |
|-----|-----|-----|-----|-----|-----|-----|-----|-----|-----|-----|-----|-----|-----|-----|
| Ser | Ser | Gly | Met | Cys<br>35 | Val | Gly | Trp | Ile | Arg<br>40 | Gln | Pro | Pro | Gly | Lys<br>45 |
| Ala | Leu | Glu | Trp | Leu<br>50 | Ala | Asp | Ile | Glu | Trp<br>55 | Asp | Asp | Asp | Lys | Asp<br>60 |
| Tyr | Asn | Thr | Ser | Leu<br>65 | Asp | Thr | Arg | Leu | Thr<br>70 | Ile | Ser | Lys | Asp | Thr<br>75 |
| Ser | Lys | Asn | Gln | Val<br>80 | Val | Leu | Thr | Val | Thr<br>85 | Asn | Met | Asp | Pro | Ala<br>90 |
| Asp | Thr | Ala | Thr | Tyr<br>95 | Tyr | Cys | Ala | Arg | Ile<br>100 | Thr | Val | Ile | Pro | Ala<br>105 |
| Pro | Ala | Gly | Tyr | Met<br>110 | Asp | Val | Trp | Gly | Arg<br>115 | Gly | Thr | Pro | Val | Thr<br>120 |
| Val | Ser | Ser |     |     |     |     |     |     |     |     |     |     |     |     |

( 2 ) INFORMATION FOR SEQ ID NO:31:

( i ) SEQUENCE CHARACTERISTICS:
        ( A ) LENGTH: 120 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:31:

|     |     |     |     |     |     |     |     |     |     |     |     |     |     |     |
|-----|-----|-----|-----|-----|-----|-----|-----|-----|-----|-----|-----|-----|-----|-----|
| Gln | Val | Thr | Leu | Arg<br>5 | Glu | Ser | Gly | Pro | Ala<br>10 | Leu | Val | Lys | Pro | Thr<br>15 |
| Gln | Thr | Leu | Thr | Leu<br>20 | Thr | Cys | Thr | Phe | Ser<br>25 | Gly | Phe | Ser | Leu | Ser<br>30 |
| Thr | Ser | Gly | Met | Ser<br>35 | Val | Gly | Trp | Ile | Arg<br>40 | Gln | Pro | Ser | Gly | Lys<br>45 |
| Ala | Leu | Glu | Trp | Leu<br>50 | Ala | Asp | Ile | Trp | Trp<br>55 | Asp | Asp | Lys | Lys | Asp<br>60 |
| Tyr | Asn | Pro | Ser | Leu<br>65 | Lys | Ser | Arg | Leu | Thr<br>70 | Ile | Ser | Lys | Asp | Thr<br>75 |
| Ser | Lys | Asn | Gln | Val<br>80 | Val | Leu | Lys | Val | Thr<br>85 | Asn | Met | Asp | Pro | Ala<br>90 |
| Asp | Thr | Ala | Thr | Tyr<br>95 | Tyr | Cys | Ala | Arg | Ser<br>100 | Met | Ile | Thr | Asn | Trp<br>105 |
| Tyr | Phe | Asp | Val | Trp<br>110 | Gly | Ala | Gly | Thr | Thr<br>115 | Val | Thr | Val | Ser | Ser<br>120 |

( 2 ) INFORMATION FOR SEQ ID NO:32:

( i ) SEQUENCE CHARACTERISTICS:
        ( A ) LENGTH: 120 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:32:

|     |     |     |     |     |     |     |     |     |     |     |     |     |     |     |
|-----|-----|-----|-----|-----|-----|-----|-----|-----|-----|-----|-----|-----|-----|-----|
| Gln | Val | Glu | Leu | Gln<br>5 | Glu | Ser | Gly | Pro | Gly<br>10 | Ile | Leu | Gln | Pro | Ser<br>15 |
| Gln | Thr | Leu | Ser | Leu<br>20 | Thr | Cys | Ser | Phe | Ser<br>25 | Gly | Phe | Ser | Leu | Ser<br>30 |
| Thr | Ser | Gly | Met | Ser<br>35 | Val | Gly | Trp | Ile | Arg<br>40 | Gln | Pro | Ser | Gly | Glu<br>45 |
| Gly | Leu | Glu | Trp | Leu<br>50 | Ala | Asp | Ile | Trp | Trp<br>55 | Asp | Asp | Lys | Lys | Asp<br>60 |

| | | | | | | | | | | | | | | | |
|---|---|---|---|---|---|---|---|---|---|---|---|---|---|---|---|
|Tyr|Asn|Pro|Ser|Leu|Lys|Ser|Arg|Leu|Thr|Ile|Ser|Lys|Asp|Thr|
| | | | |65| | | |70| | | |75| | |
|Ser|Ser|Asn|Gln|Val|Phe|Leu|Lys|Ile|Thr|Gly|Val|Asp|Thr|Ala|
| | | | |80| | | |85| | | |90| | |
|Asp|Thr|Ala|Thr|Tyr|Tyr|Cys|Ala|Arg|Ser|Met|Ile|Thr|Asn|Trp|
| | | | |95| | | |100| | | |105| | |
|Tyr|Phe|Asp|Val|Trp|Gly|Ala|Gly|Thr|Thr|Val|Thr|Val|Ser|Ser|
| | | | |110| | | |115| | | |120| | |

(2) INFORMATION FOR SEQ ID NO:33:

(i) SEQUENCE CHARACTERISTICS:
        (A) LENGTH: 95 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:33:

| | | | | | | | | | | | | | | | |
|---|---|---|---|---|---|---|---|---|---|---|---|---|---|---|---|
|Asp|Ile|Gln|Met|Thr|Gln|Ser|Pro|Ser|Thr|Leu|Ser|Ala|Ser|Val|
| | | | |5| | | |10| | | |15| | |
|Gly|Asp|Arg|Val|Thr|Ile|Thr|Cys|Arg|Ala|Ser|Gln|Ser|Ile|Ser|
| | | | |20| | | |25| | | |30| | |
|Ser|Trp|Leu|Ala|Trp|Tyr|Gln|Gln|Lys|Pro|Gly|Lys|Ala|Pro|Lys|
| | | | |35| | | |40| | | |45| | |
|Leu|Leu|Ile|Tyr|Asp|Ala|Ser|Ser|Leu|Glu|Ser|Gly|Val|Pro|Ser|
| | | | |50| | | |55| | | |60| | |
|Arg|Phe|Ser|Gly|Ser|Gly|Ser|Gly|Thr|Glu|Phe|Thr|Leu|Thr|Ile|
| | | | |65| | | |70| | | |75| | |
|Ser|Ser|Leu|Gln|Pro|Asp|Asp|Phe|Ala|Thr|Tyr|Tyr|Cys|Gln|Gln|
| | | | |80| | | |85| | | |90| | |
|Tyr|Asn|Ser|Tyr|Ser| | | | | | | | | | |
| | | | |95| | | | | | | | | | |

(2) INFORMATION FOR SEQ ID NO:34:

(i) SEQUENCE CHARACTERISTICS:
        (A) LENGTH: 106 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:34:

| | | | | | | | | | | | | | | | |
|---|---|---|---|---|---|---|---|---|---|---|---|---|---|---|---|
|Asp|Ile|Gln|Met|Thr|Gln|Ser|Pro|Ser|Thr|Leu|Ser|Ala|Ser|Val|
| | | | |5| | | |10| | | |15| | |
|Gly|Asp|Arg|Val|Thr|Ile|Thr|Cys|Lys|Cys|Gln|Leu|Ser|Val|Gly|
| | | | |20| | | |25| | | |30| | |
|Tyr|Met|His|Trp|Tyr|Gln|Gln|Lys|Pro|Gly|Lys|Ala|Pro|Lys|Leu|
| | | | |35| | | |40| | | |45| | |
|Trp|Ile|Tyr|Asp|Thr|Ser|Lys|Leu|Ala|Ser|Gly|Val|Pro|Ser|Arg|
| | | | |50| | | |55| | | |60| | |
|Phe|Ser|Gly|Ser|Gly|Ser|Gly|Thr|Glu|Phe|Thr|Leu|Thr|Ile|Ser|
| | | | |65| | | |70| | | |75| | |
|Ser|Leu|Gln|Pro|Asp|Asp|Phe|Ala|Thr|Tyr|Tyr|Cys|Phe|Gln|Gly|
| | | | |80| | | |85| | | |90| | |
|Ser|Gly|Tyr|Pro|Phe|Thr|Phe|Gly|Gly|Gly|Thr|Lys|Leu|Glu|Ile|
| | | | |95| | | |100| | | |105| | |
|Lys| | | | | | | | | | | | | | |

( 2 ) INFORMATION FOR SEQ ID NO:35:

( i ) SEQUENCE CHARACTERISTICS:
        ( A ) LENGTH: 106 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:35:

```
Asp Ile Gln Leu Thr Gln Ser Pro Ala Ile Met Ser Ala Ser Pro
                  5                  10                 15
Gly Glu Lys Val Thr Met Thr Cys Ser Ala Ser Ser Ser Val Gly
                 20                  25                 30
Tyr Met His Trp Tyr Gln Gln Lys Ser Ser Thr Ser Pro Lys Leu
                 35                  40                 45
Trp Ile Tyr Asp Thr Ser Lys Leu Ala Ser Gly Val Pro Gly Arg
                 50                  55                 60
Phe Ser Gly Ser Gly Ser Gly Asn Ser Tyr Ser Leu Thr Ile Ser
                 65                  70                 75
Ser Ile Gln Ala Glu Asp Val Ala Thr Tyr Tyr Cys Phe Gln Gly
                 80                  85                 90
Ser Gly Tyr Pro Phe Thr Phe Gly Gly Gly Thr Lys Leu Glu Ile
                 95                  100                105
Lys
```

( 2 ) INFORMATION FOR SEQ ID NO:36:

( i ) SEQUENCE CHARACTERISTICS:
        ( A ) LENGTH: 63 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:36:

GCCTGAGCTC ACGGTGACCG TGGTCCCGCC GCCCCAGACA TCGAAGTAGC AGTTCGTGAT CA    63

( 2 ) INFORMATION FOR SEQ ID NO:37:

( i ) SEQUENCE CHARACTERISTICS:
        ( A ) LENGTH: 79 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:37:

GTTGGTGACT TTAAGGACCA CCTGGTTTTT GGAGGTATCC TTGGAGATTG TGAGCCGGCT    60

CTTCAGCCAT GGATTATAG    79

( 2 ) INFORMATION FOR SEQ ID NO:38:

( i ) SEQUENCE CHARACTERISTICS:
        ( A ) LENGTH: 89 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:38:

GCGCCTTCCC TGGGGGCTGA CGAATCCAGC CTACACTCAT ACCAGAAGTG CTCAGTGAAA 60

ACCCAGAGAA GGTGGAGGTC AGTGTGAGG 89

( 2 ) INFORMATION FOR SEQ ID NO:39:

( i ) SEQUENCE CHARACTERISTICS:
        ( A ) LENGTH: 70 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:39:

CCAGGTCACC TTAAGGGAGT CTGGTCCTGC GCTGGTGAAA CCCACACAGA CCCTCACACT 60

GACCTGCACC 70

( 2 ) INFORMATION FOR SEQ ID NO:40:

( i ) SEQUENCE CHARACTERISTICS:
        ( A ) LENGTH: 78 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:40:

CAGCCCCCAG GGAAGGCCCT GGAGTCGCTT GCAGACATTT GGTGGGATGA CAAAAAGGAC 60

TATAATCCAT CCCTGAAG 78

( 2 ) INFORMATION FOR SEQ ID NO:41:

( i ) SEQUENCE CHARACTERISTICS:
        ( A ) LENGTH: 64 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:41:

GGTCCTTAAA GTGACCAACA TGGACCCTGC TGATACTGCC ACTTACTACT GTGCTCGGTC 60

TATG 64

( 2 ) INFORMATION FOR SEQ ID NO:42:

( i ) SEQUENCE CHARACTERISTICS:
        ( A ) LENGTH: 72 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:42:

GGCGTCGACT CACCATGGAC TGGACCTGGA GGGTCTTCTG CTTGCTGGCT GTAGCACCAG 60

GTGCCCACTC CC 72

( 2 ) INFORMATION FOR SEQ ID NO:43:

( i ) SEQUENCE CHARACTERISTICS:
        ( A ) LENGTH: 7 AMINO ACIDS
        ( B ) TYPE: AMINO ACID
        ( D ) TOPOLOGY: LINEAR (i i) MOLECULE TYPE: PROTEIN (x i) SEQUENCE DESCRIPTION: SEQ ID NO:43:

Thr Ser Gly Met Ser Val Gly
                    5

(2) INFORMATION FOR SEQ ID NO:44:

(i) SEQUENCE CHARACTERISTICS:
        (A) LENGTH: 16 AMINO ACIDS
        (B) TYPE: AMINO ACID
        (D) TOPOLOGY: LINEAR (i i) MOLECULE TYPE: PROTEIN (x i) SEQUENCE DESCRIPTION: SEQ ID NO:44:

Asp Ile Trp Trp Asp Asp Lys Lys Asp Tyr Asn Pro Ser Leu Lys Ser
                 5                  10                 15

(2) INFORMATION FOR SEQ ID NO:45:

(i) SEQUENCE CHARACTERISTICS:
        (A) LENGTH: 10 AMINO ACIDS
        (B) TYPE: AMINO ACID
        (D) TOPOLOGY: LINEAR (i i) MOLECULE TYPE: PROTEIN (x i) SEQUENCE DESCRIPTION: SEQ ID NO:45:

Ser Met Ile Thr Asn Trp Tyr Phe Asp Val
                 5                  10

(2) INFORMATION FOR SEQ ID NO:46:

(i) SEQUENCE CHARACTERISTICS:
        (A) LENGTH: 10 AMINO ACIDS
        (B) TYPE: AMINO ACID
        (D) TOPOLOGY: LINEAR (i i) MOLECULE TYPE: PROTEIN (x i) SEQUENCE DESCRIPTION: SEQ ID NO:46:

Lys Cys Gln Leu Ser Val Gly Tyr Met His
                 5                  10

(2) INFORMATION FOR SEQ ID NO:47:

(i) SEQUENCE CHARACTERISTICS:
        (A) LENGTH: 6 AMINO ACIDS
        (B) TYPE: AMINO ACID
        (D) TOPOLOGY: LINEAR (i i) MOLECULE TYPE: PROTEIN (x i) SEQUENCE DESCRIPTION: SEQ ID NO:47:

Thr Ser Lys Leu Ala Ser
                 5

(2) INFORMATION FOR SEQ ID NO:48:

(i) SEQUENCE CHARACTERISTICS:
        (A) LENGTH: 8 AMINO ACIDS
        (B) TYPE: AMINO ACID
        (D) TOPOLOGY: LINEAR (i i) MOLECULE TYPE: PROTEIN (x i) SEQUENCE DESCRIPTION: SEQ ID NO:48:

-continued

```
Phe  Gln  Gly  Ser  Gly  Tyr  Pro  Phe
               5
```

( 2 ) INFORMATION FOR SEQ ID NO:49:

( i ) SEQUENCE CHARACTERISTICS:
        ( A ) LENGTH: 6 AMINO ACIDS
        ( B ) TYPE: AMINO ACID
        ( D ) TOPOLOGY: LINEAR ( i i ) MOLECULE TYPE: PROTEIN ( x i ) SEQUENCE DESCRIPTION: SEQ ID NO:49:

```
Ser  Val  Gly  Tyr  Met  His
                5
```

What is claimed is:

1. A neutralizing antibody against RSV, comprising:

a human constant region and a variable region, said variable region comprising heavy and light chain framework regions and heavy and light chain CDRs, at least a portion of the heavy and light chain framework regions being derived from a human antibody, said neutralizing antibody against respiratory syncytial virus binding to the same epitope as an antibody comprising three heavy chain CDRs comprising amino acids 31–37, 52–67 and 100–109 of SEQ ID NO:31, and three light-chain CDRs comprising amino acids 24–33, 51–56 and 89–96 of SEQ ID NO:34.

2. The neutralizing antibody of claim 1 wherein the heavy chain framework comprises the heavy chain framework of SEQ ID NO. 31.

3. The neutralizing antibody of claim 1 wherein the light chain framework comprises the light chain framework of SEQ ID NO:34.

4. The neutralizing antibody of claim 1 wherein the light chain framework comprises the light chain framework of SEQ. ID NO. 34 and the heavy chain framework comprises the heavy chain framework of SEQ ID NO:31.

5. The neutralizing antibody of claim 1 wherein the heavy chain of the neutralizing antibody comprises the polypeptide of SEQ. ID NO:31.

6. The neutralizing antibody of claim 1 wherein the light chain of the neutralizing antibody comprises the polypeptide of SEQ. ID NO:34.

7. The neutralizing antibody of claim 1 wherein the heavy chain of the neutralizing antibody comprises SEQ ID NO:31 and the light chain of the antibody comprises SEQ ID NO:34.

8. A neutralizing antibody against respiratory syncytial virus, comprising:

a human constant region and a heavy and light chain variable region, said heavy and light chain variable region comprising heavy and light chain framework regions and heavy and light chain CDRs, at least a portion of the heavy and light chain framework regions being derived from a human antibody, said CDRs comprising three heavy-chain CDRs comprising amino acids 31–37, 52–67 and 100–109 of SEQ ID NO:31 and three light-chain CDRs comprising amino acids 24–33, 51–56 and 89–96 of SEQ ID NO:34.

9. A pharmaceutical composition comprising:
(a) the neutralizing antibody of claim 1 and
(b) a pharmaceutically acceptable diluent.

10. A pharmaceutical composition comprising:
(a) the neutralizing antibody of claim 2 and
(b) a pharmaceutically acceptable diluent.

11. A pharmaceutical composition comprising:
(a) the neutralizing antibody of claim 3 and
(b) a pharmaceutically acceptable diluent.

12. A pharmaceutical composition comprising:
(a) the neutralizing antibody of claim 4 and
(b) a pharmaceutically acceptable diluent.

13. A pharmaceutical composition comprising:
(a) the neutralizing antibody of claim 5 and
(b) a pharmaceutically acceptable diluent.

14. A pharmaceutical composition comprising:
(a) the neutralizing antibody of claim 6 and
(b) a pharmaceutically acceptable diluent.

15. A pharmaceutical composition comprising:
(a) the neutralizing antibody of claim 7 and
(b) a pharmaceutically acceptable diluent.

16. A pharmaceutical composition comprising:
(a) the neutralizing antibody of claim 8 and
(b) a pharmaceutically acceptable diluent.

17. A process for treating or preventing respiratory syncytial virus infection in a human, comprising:
administering to a human the neutralizing antibody of claim 1.

18. A process for treating or preventing respiratory syncytial virus infection in a human, comprising:
administering to a human the neutralizing antibody of claim 2.

19. A process for treating or preventing respiratory syncytial virus infection in a human, comprising:
administering to a human the neutralizing antibody of claim 3.

20. A process for treating or preventing respiratory syncytial virus infection in a human, comprising:
administering to a human the neutralizing antibody of claim 4.

21. A process for treating or preventing respiratory syncytial virus infection in a human, comprising:
administering to a human the neutralizing antibody of claim 5.

22. A process for treating or preventing respiratory syncytial virus infection in a human, comprising:
administering to a human the neutralizing antibody of claim 6.

23. A process for treating or preventing respiratory syncytial virus infection in a human, comprising:

administering to a human the neutralizing antibody of claim 7.

24. A process for treating or preventing respiratory syncytial virus infection in a human, comprising:

administering to a human the neutralizing antibody of claim 8.

25. The neutralizing antibody of claim 8 wherein the heavy chain framework comprises the heavy chain framework of SEQ ID NO. 31.

26. The neutralizing antibody of claim 8 wherein the light chain framework comprises the light chain framework of SEQ ID NO:34.

27. A process for treating or preventing respiratory syncytial virus infection in a human, comprising:

administering to a human the antibody of claim 25.

28. A process for treating or preventing respiratory syncytial virus infection in a human, comprising:

administering to a human the antibody of claim 26.

29. A pharmaceutical composition comprising:

(a) the neutralizing antibody of claim 25 and (b) a pharmaceutically acceptable diluent.

30. A pharmaceutical composition comprising:

(a) the neutralizing antibody of claim 26 and (b) a pharmaceutically acceptable diluent.

* * * * *

UNITED STATES PATENT AND TRADEMARK OFFICE
CERTIFICATE OF CORRECTION

PATENT NO. : 5,824,307
DATED : October 20, 1998
INVENTOR(S) : Leslie Sydnor Johnson It is certified that error appears in the above-identified patent and that said Letters Patent is hereby corrected as shown below:

On the title page, item [54], title of invention, should read
-- NEUTRALIZING ANTIBODY AGAINST RESPIRATORY SYNCYTIAL VIRUS F ANTIGEN --

In Claim No. 27, Column 44, Line 1: After the phrase "to a human the," the word --neutralizing-- should be inserted.

In Claim No. 28, Column 44, Line 4: After the phrase "to a human the," the word --neutralizing-- should be inserted.

Signed and Sealed this

Thirtieth Day of March, 1999

Attest:

Q. TODD DICKINSON

*Attesting Officer*   Acting Commissioner of Patents and Trademarks

UNITED STATES PATENT AND TRADEMARK OFFICE
CERTIFICATE OF CORRECTION

PATENT NO. : 5,824,307
DATED : October 20, 1998
INVENTOR(S) : Leslie Sydnor Johnson It is certified that error appears in the above-identified patent and that said Letters Patent is hereby corrected as shown below:

On the title page, item

[75] Inventor: Leslie Sydnor Johnson, Germantown, Md.

Signed and Sealed this

Sixth Day of April, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO.   : 5,824,307
DATED        : October 20, 1998
INVENTOR(S)  : Leslie Sydnor Johnson It is certified that error appears in the above-identified patent and that said Letters Patent is hereby corrected as shown below:

<u>Column 15,</u>
Line 15, in the table entitled "Kinetic Constants for RSV Mabs", and in the column with the heading "$k_a(assoc)M^{-1} sec^{-1}$" change " $5.0 \times 10^{-5}$
$4.9 \times 10^{-4}$
$3.5 \times 10^{-4}$
$3.5 \times 10^{-4}$
$2.2 \times 10^{-4}$"

to

-- $5.0 \times 10^4$
$4.9 \times 10^4$
$3.5 \times 10^4$
$3.5 \times 10^4$
$2.2 \times 10^4$ --

Signed and Sealed this

Eleventh Day of February, 2003

JAMES E. ROGAN
*Director of the United States Patent and Trademark Office*